United States Patent
Tan et al.

(10) Patent No.: US 9,067,017 B2
(45) Date of Patent: Jun. 30, 2015

(54) FLOW SYSTEM OF A DIALYSIS DEVICE AND A PORTABLE DIALYSIS DEVICE

(75) Inventors: Kim Cheng Tan, Singapore (SG); Christian Gert Bluchel, Singapore (SG); Lay Leng Chew, Singapore (SG); Kee Kiat Chua, Singapore (SG); Lai Ching Helen Ho, Singapore (SG); Keng Hong Lee, Singapore (SG); Liutong Lin, Singapore (SG); Weng Cheong Roy Tang, Singapore (SG); Keng Mun Yue, Singapore (SG); Kim Jyh Wong, Singapore (SG); Cheng Lam Chua, Singapore (SG)

(73) Assignee: TEMASEK POLYTECHNIC, Singapore (SG)

( * ) Notice: Subject to any disclaimer, the term of this patent is extended or adjusted under 35 U.S.C. 154(b) by 644 days.

(21) Appl. No.: 13/000,830

(22) PCT Filed: Jun. 22, 2009

(86) PCT No.: PCT/SG2009/000230
§ 371 (c)(1),
(2), (4) Date: Apr. 4, 2011

(87) PCT Pub. No.: WO2009/157878
PCT Pub. Date: Dec. 30, 2009

(65) Prior Publication Data
US 2011/0184340 A1  Jul. 28, 2011

Related U.S. Application Data

(60) Provisional application No. 61/074,997, filed on Jun. 23, 2008.

(51) Int. Cl.
*A61M 1/00* (2006.01)
*A61M 1/16* (2006.01)
(Continued)

(52) U.S. Cl.
CPC ............. *A61M 1/1696* (2013.01); *A61M 1/28* (2013.01); *B01J 20/06* (2013.01); *B01J 20/20* (2013.01);
(Continued)

(58) Field of Classification Search
CPC ............ B01J 39/12; B01J 41/10; B01J 20/06; B01J 20/20; B01J 20/22; B01J 20/28052; A61M 1/1696; A61M 1/28
USPC ...................................................... 604/28–31
See application file for complete search history.

(56) References Cited

U.S. PATENT DOCUMENTS 4,240,408 A   12/1980 Schael
5,141,493 A   8/1992  Jacobsen et al.
(Continued)

FOREIGN PATENT DOCUMENTS

JP   2000-084070 A   3/2000
WO   95/35124 A1     12/1995
WO   2004/009156 A2  1/2004

OTHER PUBLICATIONS

International Search Report: PCT/SG2009/000230.
(Continued)

*Primary Examiner* — Kami A Bosworth
*Assistant Examiner* — Imani Hayman
(74) *Attorney, Agent, or Firm* — Ladas & Parry LLP

(57) ABSTRACT

There is provided a flow system of a dialysis device including a dialysate conduit which is capable of being in fluid communication with the peritoneal cavity of a patient's body and of being in fluid communication with a flow path, the flow path allowing dialysate to flow from a patient's body to a sorbent capable of removing contaminants within the dialysate in an outflow mode and in an inflow mode returning the dialysate substantially free of contaminants to the patient's body. The device also includes a pump for moving the dialysate along the flow path in both the outflow mode and inflow mode and a plurality of valves disposed along the flow path. There is also provided a portable dialysis device.

26 Claims, 20 Drawing Sheets

(51) Int. Cl.
   *B01J 20/06* (2006.01)
   *B01J 20/20* (2006.01)
   *B01J 20/22* (2006.01)
   *B01J 20/28* (2006.01)
   *B01J 39/12* (2006.01)
   *B01J 41/10* (2006.01)
   *A61M 1/28* (2006.01)

(52) U.S. Cl.
   CPC ............ *B01J 20/22* (2013.01); *B01J 20/28052* (2013.01); *B01J 39/12* (2013.01); *B01J 41/10* (2013.01)

(56) References Cited

U.S. PATENT DOCUMENTS

| | | | |
|---|---|---|---|
| 5,350,357 A | | 9/1994 | Kamen et al. |
| 5,641,405 A | * | 6/1997 | Keshaviah et al. ............ 210/645 |
| 6,168,578 B1 | | 1/2001 | Diamond |
| 6,595,948 B2 | | 7/2003 | Suzuki et al. |
| 2003/0114787 A1 | | 6/2003 | Gura |
| 2007/0179431 A1 | * | 8/2007 | Roberts et al. ................. 604/29 |
| 2009/0124963 A1 | * | 5/2009 | Hogard et al. .................. 604/30 |
| 2010/0004588 A1 | * | 1/2010 | Yeh et al. ........................ 604/28 |
| 2012/0022441 A1 | * | 1/2012 | Kelly et al. ..................... 604/29 |
| 2013/0131582 A1 | * | 5/2013 | Childers et al. ................ 604/28 |

OTHER PUBLICATIONS

Australian Office Action issued Jun. 3, 2013; Appln. No. 2009263046.
Chinese Office Action dated Apr. 3, 2013; Appln. No. 200980131854.0.
Japanese Office Action dated Jul. 12, 2013; Appln. No. 2011-516228.
New Zealand Office Action dated Nov. 16, 2012; Patent Appln. No. 590471.
Russian Office Action Jul. 1, 2013; Appln. No. 2011102163/14(002869).

* cited by examiner

FLOW SYSTEM OF A DIALYSIS DEVICE AND A PORTABLE DIALYSIS DEVICE

TECHNICAL FIELD

The present invention relates to a flow system for use in the dialysis device and a portable dialysis device containing said flow system.

BACKGROUND

Kidneys are vital organs of the humans homeostasis system. Kidneys act as a natural filter in the body which remove toxic metabolic wastes such as urea from the blood. Kidney failure or malfunction may lead to an accumulation of toxins and to an imbalanced electrolyte level in the blood, which may result in undesirable repercussions that are hazardous to an individual's health. In this regard, patients with impaired kidney functionality will usually have to undergo dialysis for the removal of toxic wastes in the blood and for the restoration of the optimal level of electrolytes in the blood.

For the past few years, the predominant form of dialysis used for patients with end-stage renal disease (ESRD) is hemodialysis. Hemodialysis involves the use of an extracorporeal system for the removal of toxins directly from the patient's blood by passing a large amount of the patient's blood through a filtering unit or dialyzer. In conventional hemodialysis processes, patients must spend hours immobilized throughout the duration of the dialysis, encumbering the patient's mobility. Another drawback of hemodialysis is the need to utilize an anticoagulant during the treatment process, which may inevitably increase the risk of internal hemorrhages.

The other form of dialysis used for patient with kidney failure is peritoneal dialysis, most commonly applied in the following two techniques: "continuous ambulatory peritoneal dialysis" (CAPD) and "automated peritoneal dialysis" (APD). In CAPD, fresh dialysate is infused into the patient's abdominal (peritoneal) cavity where, by means of diffusion, metabolic waste and electrolytes in the blood are exchanged with the dialysate across the peritoneal membrane. To allow sufficient diffusion of the electrolytes and metabolic waste to occur, the dialysate is retained in the abdominal (peritoneal) cavity for a couple of hours before removal and replacement (of the spent dialysate) with fresh dialysate. Major drawbacks of continuous ambulatory peritoneal dialysis are a low level of toxin clearance, and the need to continuously replace the spent dialysate, which can be arduous for the patient and disruptive to his/her daily activities.

To overcome the above-mentioned problems of conventional hemodialysis and continuous ambulatory peritoneal dialysis treatments, automated peritoneal dialysis (APD) devices have been developed in recent years. In APD, dialysis is performed at night, or while the patient is resting. The dialysate is exchanged and replaced automatically. This allows for more frequent changes of dialysate and better toxin clearance with minimal interruption to the patient's daily activities.

However, all dialysis techniques described above still suffer from several drawbacks. For example, hemodialysis fails to remove protein-bound toxins, while peritoneal dialysis entails a significant loss of beneficial proteins for the patient. Hemodialysis CAPD and APD fail to provide optimal clearance for uremic toxins, because of limitation of application time and/or volume of dialysate used (due to cost constraints). In cases where the hemodialysis device comprises a regenerating unit, such as a sorbent that regenerates spent dialysate, the overall size and weight of these dialysis devices are often too large to be portable and therefore do not improve a patients' mobility. Such devices are also cumbersome due to the bulky nature of the sorbent used to ensure adequate removal of the toxins, which is a requirement resulting from the intermittent use of the device. In addition, the flow system of known regenerating hemodialysis devices requires a plurality of pumps, which in turn undesirably increases the overall size, weight and power consumption of the device.

There is a need to provide a flow system for a dialysis device that overcomes or at least ameliorates one or more of the disadvantages described above. There is also a need to provide a flow system for the dialysis device, which ensures proper and efficient functioning of the dialysis device without compromising on the size, weight and power consumption of the device.

SUMMARY OF INVENTION

According to a first aspect, there is provided a flow system of a dialysis device comprising:
  a dialysate conduit which is capable of being in fluid communication with the peritoneal cavity of a patient's body and of being in fluid communication with a flow path, said flow path allowing dialysate to flow from a patient's body to a sorbent capable of removing contaminants within said dialysate in an outflow mode and in an inflow mode returning said dialysate substantially free of contaminants to said patient's body;
  a pump for moving said dialysate along said flow path in both the outflow mode and inflow mode; and
  a plurality of valves disposed along said flow path and being configured to, in the outflow mode, allow said dialysate to flow from said dialysate conduit to said sorbent for removal of contaminants therein, and in the inflow mode, allow dialysate substantially free of said contaminants to flow back to said dialysate conduit for transmission to said patient's body.

Advantageously, the flow system does not require a plurality of pumps to work the dialysis device effectively. More advantageously, only a single pump is required to pump fluid to the sorbent and thereafter back to the patient's body. This significantly reduces the size and weight of the dialysis device and also saves on operating power, thereby further saving on space required for smaller battery size reflected in the embodiments in which the device is mobile and wearable. In one embodiment, the flow system comprises only one pump that is operative for both the inflow mode and the outflow mode. In another embodiment, the flow system comprises a total of one pump.

In another embodiment, there is provided a flow system of a dialysis device comprising:
  a flow path for allowing dialysate to flow from a patient's body to a sorbent capable of removing contaminants within said dialysate, and back to said patient's body;
  a pump for moving said dialysate along said flow path; and
  a series of valves disposed along said flow path and being configured to, in an outflow mode, allow said dialysate to flow to said sorbent for removal of contaminants therein, and in an inflow mode, allow dialysate substantially free of said contaminants to flow back towards said patient's body,
  wherein the pump moves said dialysate fluid along said flow path in both said sorbent mode and in said inflow mode. In one embodiment, the flow path allows dialysate to flow from a patient's peritoneal cavity to a sorbent capable of removing contaminants within said dialysate, and back to said patient's peritoneal cavity.

In one embodiment, the flow system further comprises a fibrin filter means disposed along the flow path to, in an outflow mode, remove fibrin from dialysate before said dialysate enters said pump, said plurality of vales and said sorbent. The fibrin filter means may be disposed on said flow path adjacent to said dialysate conduit. For example, the fibrin filter means may be disposed between the patient's body and the pump and along said flow path. In one embodiment, the fibrin filter means is disposed immediately adjacent to the patient's body for example at the exit of the peritoneal cavity. Advantageously, the fibrin filter means is able of removing fibrin present in mucus or forms of coagulation arising from the peritoneal cavity before the dialysate enters the flow system. This advantageously reduces the risk of clogging of the flow system. More advantageously, filtering off fibrin containing material prolongs the lifespan of the flow system. The fibrin filter means may be a filtration device, a filter paper or any means suitable for filtering away fibrin containing material in the dialysate.

The flow system may further comprise a micro-organism filter means being disposed along said flow path, said micro-organism filter means being configured to remove microorganisms from the dialysate when transmitted along the flow path. The micro-organism filter means may be disposed along the flow path between the pump and dialysate conduit. The micro-organism filter means may be a bacteria filter capable of removing bacteria from the dialysate. The filter means also serves to remove any microorganisms that have inadvertently entered the flow system. As the flow system works to regenerate and reconstitute spent dialysate, the presence of a micro-organism filter means for filtering microorganisms from the dialysate ensures the sterility of the dialysate returning to the patient's body. The micro-organism filter means may be a filtration device, a filter paper or any means suitable for filtering away fibrin containing material in the dialysate.

In one embodiment, the flow system further comprises a pump module having said pump and part of said flow path disposed therein, said pump module being capable of being coupled to a patient's body; and a sorbent module capable of being reversibly attached to the pump module and having the sorbent and the other part of the flow path disposed therein, wherein when the sorbent module is attached to said pump module, the flow path of the sorbent module is in fluid communication with the flow path of the pump module. Advantageously, the sorbent module containing the sorbent can be replaced easily when the sorbent contained therein is spent. This greatly improves the ease of usage and convenience to the user. The sorbent module can be easily reattached to the rest of the flow system of the pump module via a connector. Thus, at least part of said flow path may be contained in a detachable sorbent module containing said sorbent that is capable of being fluidly decoupled from said pump in an inoperative mode.

The flow system may further comprise gas vent means disposed along said flow path for removing gas from the dialysate. In one embodiment, the gas vent means comprises a sorbent gas vent downstream of the sorbent in the outflow mode, for removing gas from the dialysate that has been generated by contact with the sorbent. Advantageously, when the sorbent gas vent is disposed downstream of the sorbent in the outflow mode, the large amount of gases that are released from the sorbent when the dialysate reacts with sorbent, can be quickly and effectively released from the flow system. More advantageously, this prevents the build up of pent up gases which may undesirably increase the pressure within the flow system. The sorbent gas vent may be disposed within said sorbent module and is in fluid communication with the flow path therein. In one embodiment, the sorbent gas vent is disposed immediately adjacent to the sorbent, along said flow path for removing gas from the dialysate.

In one embodiment, the gas vent means comprises a degasser, upstream of the micro-organism filter means in the inflow mode, for removing gas from the dialysate before passing to said micro-organism filter means. The degasser may be disposed within said pump module and is in fluid communication with the flow path therein. Advantageously, when degasser is arranged to be upstream of the micro-organism filter means in the inflow mode, gases present within the dialysate can be removed before the dialysate passes through the micro-organisms filter means, such as a bacteria filter. Advantageously, as the presence of air bubbles having sizes that are larger than the pore sizes of the filter means increases the risk of damaging the filter means, the presence of the degasser upstream of the micro-organism filter means in the inflow mode reduces such risk by eliminating gases in the dialysate before the dialysate passes through the filter means. In one embodiment, the degasser disclosed herein may have antibacterial functionality. For example, the degasser may also be fitted with an additional filter to prevent microorganisms such as bacteria from entering the flow system from the atmosphere. The degasser may be disposed immediately adjacent to the micro-organisms filter means. The gas vent means disclosed herein may also be replaced any means capable of removing gases from the flow system.

In one embodiment, the flow system further comprises a controller that is configured to actuate the pump for operation in the inflow mode and outflow mode. The controller may be disposed in said pump module to ensure compactness. In one embodiment, the controller is electrically coupled to a power source, such as a cell or a battery located in said pump module. The controller may also be electrically coupled directly to electrical mains. The controller may also be configured to actuate the plurality of valves for transmission of dialysate along said flow path, wherein the valves are selected from the group consisting of at least one of a pinch valve, a shuttle valve, a piloted valve and a solenoid valve. This allows the inflow and outflow of the dialysate from the patient's body to be automatic. This is particularly useful when valves such as a pinch valves are used to control the flow of dialysate.

In another embodiment, the plurality of valves is operative by the flow direction of dialysate in along said flow path. Such valves may be check valves. Advantageously, when check valves are used, the flow system can operate without the need of additional types of valves such as pinch valves.

In one embodiment, the flow system further comprises a sensor for sensing the amount of dialysate being transmitted from the dialysate conduit in at least one of the inflow mode and outflow mode. The controller may be configured to determine the amount of dialysate being sensed by the sensor and thereby change the speed of the operation of the pump according to the sensed dialysate load.

In one embodiment, the pump is configured to move dialysate along the flow path without any moving parts of the pump coming into contact with the dialysate. The pump may pump is at least one of a peristaltic pump and a diaphragm pump. Advantageously, when peristaltic pumps or diaphragm pumps are used, there are no moving mechanical components in contact with the dialysate. This enables the flow system to be a closed loop system and because there is no contact of the dialysate with any moving mechanical components, the risk of contamination of the dialysate is substantially reduced. Preferably, the pump can achieve a dialysate flow rate of from 0.1 l/hr to 20 l/hr. Advantageously, this range of flow rate is found by the inventors to effectively and efficiently remove contaminants from the dialysate.

In one embodiment, the flow system further comprises an additive dispensing means for dispensing a desired additive into the dialysate. The dispensing means may comprise a dispenser disposed in said sorbent module and being in fluid communication with said flow path for addition of said additive thereto. The dispenser may be actuated by said controller to modulate the amount of additive to said dialysate according to the flow rate thereof. The addition of additives into the dialysate serves to beneficially reconstitute nutrients which have been lost from the dialysate during dialysis.

The flow system may further comprise a storage chamber in fluid communication with said flow path, said storage module configured to store dialysate that is substantially free of contaminants which have been removed by said sorbent. The storage chamber may be disposed in the sorbent module In yet another embodiment, the flow system further comprises an ammonia sensor configured to detect ammonia present in said dialysate before passage to said dialysate conduit in an inflow mode. Advantageously, the sensor for detecting ammonia present in the dialysate maximizes the utilization of the sorbent before the sorbent has to be replaced. Due to the presence of the sensor, the patient will be able to accurately identify when the sorbent of the flow system has to be replaced. More advantageously, because usage of the sorbent of the flow system can be fully maximized, there is no need to incorporate excessive sorbent material within the flow system as a precautionary measure; such excessive sorbent material may ultimately be under-utilized. Accordingly, because there is no need to incorporate excessive sorbent material, the entire flow system and dialysis device can be kept compact and there is also reduced wastage of material due to under-utilization. The ammonia sensor may be disposed in the pump module.

According to a second aspect, there is provided a portable dialysis device comprising:
 a housing having means for attachment to a patient's body, the housing comprising:
 a dialysate conduit which is capable of being in fluid communication with the peritoneal cavity of a patient's body and of being in fluid communication with a flow path, said flow path allowing dialysate to flow from a patient's body to a sorbent capable of removing contaminants within said dialysate in an outflow mode and in an inflow mode returning said dialysate substantially free of contaminants to said patient's body;
 a pump for moving said dialysate along said flow path in both the outflow mode and inflow mode; and
 a plurality of valves disposed along said flow path and being configured to, in the outflow mode, allow said dialysate to flow from said dialysate conduit to said sorbent for removal of contaminants therein, and in the inflow mode, allow dialysate substantially free of said contaminants to flow back to said dialysate conduit for transmission to said patient's body. The portable dialysis device may be attached to the patient's body and transported by the patient easily.

In one embodiment, the means for attachment are configured to attach the dialysis device to the torso of the patient. Advantageously, the dialysis device can be transported easily by the patient and allows the patient to carry out his/her normal daily activities without substantial impediment while having dialysis occurring simultaneously. In one embodiment, the means for attachment comprises a belt configured to engage the waist of the lower torso or hips of the patient. In another embodiment, the means for attachment comprises a back-pack capable of being worn by the patient, said back-pack having a pouch for receipt of said housing. This may enable the weight of the dialysis device to be distributed throughout the large area of the upper torso of the patient, thereby improving user comfort.

The portable dialysis device disclosed herein may also further comprise any of the components described above for the flow system.

In a third aspect, there is provided the portable dialysis device to treat a patient suffering from kidney malfunction, for example renal failure or renal related diseases.

Definitions

The following words and terms used herein shall have the meaning indicated:

The term "sorbent" as used herein broadly refers to a class of materials characterized by their ability to adsorb and/or absorb the desired matter of interest.

The term "non-toxic" as used herein refers to a substance that causes little to no adverse reactions when present in the human body.

The term "contaminants" in the context of this specification, means any constituents, typically toxic constituents, within a dialysate that are generally harmful to human health and which are desirable to be removed in a dialysate detoxification process. Typical contaminants include, but are not limited to ammonium, phosphates, urea, creatinine and uric acid.

The term "biocompatible" as used herein refers to the property of a material that does not cause adverse biological reactions to the human or animal body.

The term "upstream" as used herein refers to a localization within the flow path, relative to a point of reference, and in direction opposite to that of the dialysate flow.

The term "downstream" as used herein refers to a localization within the flow path, relative to a point of reference, and in direction of the dialysate flow.

The term "crack-pressure" as used herein refers to the point at which the internal pressure of a pneumatic system triggers the opening of a valve.

The term "regenerate" as used herein refers to the action of detoxifying dialysate by absorption of uremic toxins.

The term "reconstitute" as used herein refers to the action of converting regenerated dialysate to essentially the same state and chemical composition as fresh peritoneal dialysate prior to dialysis.

The term "outflow mode" as used herein refers to the flow of dialysate from the patient's body through a sorbent. The flow is referenced from the patient's body.

The term "inflow mode" as used herein refers to the flow of the dialysate from a sorbent to the patient's body. The flow is referenced to the patient's body.

The term "ultrafiltration mode" as used herein refers to the flow of dialysate from the patient's body to an ultrafiltration bag. The flow is referenced to the patient's body.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range:

DETAILED DISCLOSURE OF EMBODIMENTS

Exemplary, non-limiting embodiments of a flow system of dialysis device and portable dialysis device will now be disclosed.

The flow system of a dialysis device comprises: a dialysate conduit which is capable of being in fluid communication with the peritoneal cavity of a patient's body and of being in fluid communication with a flow path, said flow path allowing dialysate to flow from a patient's body to a sorbent capable of removing contaminants within said dialysate in an outflow mode and in an inflow mode returning said dialysate substantially free of contaminants to said patient's body;
  a pump for moving said dialysate along said flow path in both the outflow mode and inflow mode; and
  a plurality of valves disposed along said flow path and being configured to, in the outflow mode, allow said dialysate to flow from said dialysate conduit to said sorbent for removal of contaminants therein, and in the inflow mode, allow dialysate substantially free of said contaminants to flow back to said dialysate conduit for transmission to said patient's body. The portable dialysis device comprises a housing having means for attachment to a patient's body, the housing comprising:
  a dialysate conduit which is capable of being in fluid communication with the peritoneal cavity of a patient's body and of being in fluid communication with a flow path, said flow path allowing dialysate to flow from a patient's body to a sorbent capable of removing contaminants within said dialysate in an outflow mode and in an inflow mode returning said dialysate substantially free of contaminants to said patient's body;
  a pump for moving said dialysate along said flow path in both the outflow mode and inflow mode; and
  a plurality of valves disposed along said flow path and being configured to, in the outflow mode, allow said dialysate to flow from said dialysate conduit to said sorbent for removal of contaminants therein, and in the inflow mode, allow dialysate substantially free of said contaminants to flow back to said dialysate conduit for transmission to said patient's body.

The valves may be configured to allow a uni-directional flow or a bi-directional flow when required. The valves may be pinch valves, shuttle valves, piloted valves, solenoid valves, check valves or combinations thereof. The flow system/dialysis device may also be linked to a controller such as a control system configured to open and close the valves in an automated manner. The opening and closing of any one of the valves may also be determined by the feedback received by the control system on the status of the other valves. The control system may also invert the pump direction. The valves may be made of a material that is biocompatible or biologically inert. In one embodiment, the valves are made up of a material that is capable of withstanding the pressure within the flow system without any appreciable change in the desired properties.

In one embodiment, the flow system/dialysis device comprises a total of only one pump.

The pump may be replaced by any means suitable for generating flow by creating a pressure differential between any two points in the flow circuit. In one embodiment, the pump is selected from the group consisting of peristaltic pumps, gear pumps, diaphragm pumps, piston pumps, hydraulic pumps, pneumatic pumps and mechanical pumps. Advantageously, due to the design of the flow system, only one pump is required, without any loss in the desired pressure required to pump the dialysate from the peritoneal cavity through the sorbent before being pumped through a series of other filters and returned back to the peritoneal cavity. In one embodiment, the pump is able to achieve a dialysate flow rate of from about 0.1 l/hr to about 20 l/hr.

The disclosed flow system/dialysis device may also be in fluid communication with a filter capable of removing fibrin from the dialysate. The removal of fibrin from the dialysate may reduce the risk of blockage in the flow system of the dialysis device. In one embodiment, the filter for removing fibrin removes fibrin from the dialysate flow, before the dialysate is fed to a sorbent. This may reduce the risk of clogging. In another embodiment, the filter for removing fibrin removes fibrin from the dialysate flow, before the dialysate enters the pump- and valve assembly. This may prevent clogging and blockage of components vital for the functionality of the flow system, such as sensors, valves and pumps, and increases the lifespan of the sorbent. In one embodiment, the filter for removing the fibrin is made of poly(vinyl)chloride (PVC). In one embodiment, the filter for removing the fibrin is made of polypropylene. The filter may also be capable of withstanding the pressure within the flow system without any appreciable change in its desired properties. The flow system/dialysis device may also be in fluid communication with a bacteria filter for removing bacteria and any micro-organisms that are present in the dialysate. In one embodiment, the bacteria filter for removing microorganisms has pore sizes of no more than about 0.20 microns.

In another embodiment, the bacteria filter has a surface area of from about 0.05 m$^2$ to about 0.60 m$^2$. The surface area of the bacteria filter may be about 0.185 m$^2$. The bacteria filter may also be capable of withstanding the pressure within the flow system without any appreciable change in its desired properties.

In one embodiment, the flow system/dialysis device is in fluid communication with at least one air vent, capable of releasing accumulated gaseous inclusions within the dialysate into the atmosphere. The release of gaseous inclusions may occur by means of a mechanical valve or a membrane valve. In one embodiment, gaseous inclusions is accumulated and released in a float valve. In another embodiment gaseous inclusions may be released through a hydrophobic semi permeable membrane of pore size of no more than 0.20 microns, wherein the hydrophobic membrane is permeable to gas, but impermeable to dialysate. In one embodiment, unwanted influx of atmospheric gases into the dialysate path is prevented by means of a suitably oriented check valve, sealing the external face of the venting membrane. In one embodiment, one of said air vents is positioned immediately next to, and downstream of the sorbent. Advantageously, the positioning of the vent in immediate vicinity of the sorbent allows for efficient release of gas inclusions and prevents overpressure, malfunction of other components within the flow system and/or the dialysis device, and harmful effects of gas inclusions for the patient. In another embodiment, one of said air vents may be positioned within the flow path immediately next to, and upstream the sterile filter. The exhaustive release of gaseous inclusions prevents clogging of the sterile filter by gaseous inclusions.

The flow system/dialysis device may also be in fluid communication with at least one gas remover (degasser).

The gas remover may be capable of removing any unwanted gases, such as carbon dioxide gas, that are produced during the dialysis operation or during dialysis regeneration in the sorbent. In one embodiment, the gas remover comprises a vent that releases the unwanted gas from the flow system. The vent may be a mechanical vent e.g. float vent. The vent may also be effected by a hydrophobic membrane, permeable to gas but impermeable to dialysate. In another embodiment, the gas remover is a hydrophobic membrane vent or a combination of hydrophobic vent and hydrophilic filter.

In one embodiment, the flow system/dialysis device is also in fluid communication with at least one dispensing system ("enrichment module") capable of supplementing desired additives into the dialysate flow. The desired substances may include essential substances for normal functioning of the human body, selected from the group consisting of potassium, calcium and magnesium. The desired substances may also include osmotic agents essential for the efficacy of dialysis, such as glucose, oligosaccharides or amino acids. In one embodiment, the desired substances include substances such as supplements, nutrients, vitamins and co-factors that generally promote human health. The desired substances may also include therapeutic substances such as medications and hormones. Advantageously, the enrichment module does not require any additional discharging or pumping mechanisms to ensure that an accurate amount of desired substances is dispensed into the dialysate. More advantageously, this reduces the overall power consumption and weight of the dialysis device.

The flow system/dialysis device may also be in fluid communication with a storage module. The storage module may be capable of storing regenerated and/or reconstituted dialysate leaving the sorbent, prior before being returned to the patient. The storage module may also be capable of storing excess dialysate ("ultrafiltrate") or additional dialysate, which may be intermittently removed from, or introduced into the patient's peritoneal cavity.

In one embodiment, the flow system/dialysis device is further in fluid communication with at least one pressure sensor. In one embodiment, the flow system/dialysis device is in fluid communication with two pressure sensors, a first pressure sensor being capable of sensing the pressure of the dialysate flow into the dialysis device and from the dialysis device, while a second pressure sensor being capable of sensing the pressure of the dialysate flow before entering the sorbent. The pressure sensor may also provide feedback input to a pressure regulator to regulate the pressure of the dialysate flowing to and from the dialysis device. The pressure sensor may also provide feedback to trigger an alarm in case the detected pressure is outside an acceptable range.

The flow system/dialysis device may also be in fluid communication with an ammonia sensor. The ammonia sensor may be situated "in-line" in the flow path for regenerated dialysate returning from the sorbent to the patient. In another embodiment, the ammonia sensor is connected "off-line", via a 3-way connector and a suitable dosage system to any point in the flow path for regenerated dialysate returning from the sorbent to the patient. In one embodiment, the ammonia sensor is capable of detecting the concentration of ammonia present in the dialysate in the form of free ammonia or ammonium ions. The ammonia sensor may also provide a feedback input to the control system of the dialysis device so that if the ammonia concentration exceeds an undesired upper limit range, the control system may activate an alarm and/or deactivate the pump.

In another embodiment, the ammonia sensor comprising a flow-through cell is situated "in-line" in the flow path for regenerated dialysate returning from the sorbent to the patient, with all of the regenerated dialysate passing through said cell.

In another embodiment, said flow-through cell is connected "off-line", via a 3-way connector and a suitable dosage system to any point in the flow path for regenerated dialysate returning from the sorbent to the patient. The dosage system may allow only a small part of the regenerated dialysate to pass through said cell. The dosage system may be comprised of a pressure regulator, an orifice, a pinch valve, a microdispense valve, or a pump. Dialysate passing through said sensor cell may be collected in a suitable container, such as a drip bag, for later disposal.

In one embodiment, the ammonia sensor is positioned in any part of the dialysate flow path downstream the cation exchanger layers of the sorbent. In one embodiment, the ammonia sensor is positioned in the dialysate flow path downstream of all cation and anion exchanger layers and upstream of an organic compound absorber layer. Advantageously, this arrangement ensures the re-adsorption of traces of harmful substances that may leak from the ammonia sensor.

In one embodiment, the ammonia sensor is also an ammonia-selective potentiometric or amperometric electrode.

In one embodiment, the flow system/dialysis device receives and/or sends feedback signals to an alarm system. The alarm system may be able to give off an audio and/or a visual alarm and may also be able to display the reason for the alarm. The alarm system may be able to give off an alarm when the pressure, volume and/or flow rate of the dialysate is not within the desired range. In another embodiment, the alarm system is able to give off an alarm when the concentrations of metabolic toxins (most notably that of ammonia) are not within the desired range. Preferably, the alarm system may also give off an alarm when any of the components of the flow system requires replacement, for example when the sorbent is spent and requires replacement. The alarm system may also be advantageously linked to the control system to give off an alarm when the power status of the dialysis device is low. In one embodiment, the alarm system also gives off an alarm when the pump current and pump angular speed are out of the normal working. range.

The control system may incorporate a processor capable of interrogating a memory having predetermined instructors for pumping dialysate from an external source to the dialysis device and from the dialysis device back to the external source. The control system may be linked to a user interface, such as a keyboard, and a graphical user interface, such as an LCD display, for allowing an operator to interact with the control system.

In one embodiment, the control system comprises a memory having a computer algorithm for storing said predetermined instructions. The control system may also comprise a removable storage device such as a Secure Digital (SD) card to capture and log key information of the dialysis device and the patient. Advantageously, the LCD display linked to the control system is touch sensitive and is capable of relaying a user's instructions to the other components of the control system.

The control system may control the delivery of the fresh dialysate to the peritoneal cavity and the spent dialysate from the peritoneal cavity. The control system may also control the timing, during and amount of each delivery of the dialysate. The control system may receive feedback from the pressure sensor and ammonia sensor.

The control system may be able to store the delivery history of the dialysate. The control means may be able to store and process the dialysate dispensing out parameters (i.e amount and duration) inputted by a user. The control system may also be capable of controlling the dispensing output of the desired substance to be discharged into the dialysate from the enrichment module.

Various algorithms can be used in order to control the dispensing output. The system may use a predetermined program setting values as a starting point and over time these settings can be customized according to the user's requirements.

Advantageously, the control system has a learning ability to allow it to call on prior knowledge or memory to apply instantaneous settings. This learning ability is preferably encoded by software. The prior knowledge, or stored history, is based on past events, including dispensing rates and dispensing periods, and is stored in the memory. The dialysis system itself may be monitored remotely by a hard wired communication link to the control means, or by radio communications or by means of a portable data log off.

The flow system/dialysis device may be powered by a alternating (A.C) power supply or a directly current (D.C) power supply. In one embodiment, when the flow system/dialysis device can only be powered by a D.C power supply, the flow system/dialysis device may further comprise a rectifier to rectify the current originating from a A.C power supply. In one embodiment, the flow system is powered by compact batteries to ensure portability. In one embodiment, the flow system is powered by a rechargeable battery that is capable of powering the flow system/dialysis device for at least eight hours of continuous usage. The conduits through which the dialysate flows may be made of resilient, chemically and biologically inert materials.

The conduits may also be able to withstand the pressure with the flow system of the dialysis device without leakage. In one embodiment, the conduits are tubings made of medical grade polymer such as nylon, silicone or polyurethane. The tubings and the other components of the flow system may also be connected using a connector made of resilient material such as of medical grade polymer as nylon or polycarbonate or polysulphone. In another embodiment, at least one connector has a double-lock quick release and iodine cap features to prevent leakage, spillage and bacteria contamination.

The flow system/dialysis device may also be mounted on a carrier that has a wearable configuration so that the dialysis device comprising the flow system can be easily transported by the user. The carrier with a wearable configuration may allow the patient to have continuous peritoneal dialysis when stationary or on the move. Advantageously, the carrier allows patient free movement and does not restrict the patient's normal range of motion undesirably. In one embodiment, the carrier is made of a material that is light weight, fire resistant and water proof (non-water absorbing). The carrier may also be made up of a material that is sufficiently hard enough to protect the components and tubings of the dialysis device from knocks and accidental pinching. In one embodiment, the carrier is ergonomically designed to distribute the weight of the dialysis device so that the pressure arising from the weight of the dialysis device is distributed over the users' body, preventing excessive pressure concentrations in specific parts of the user's body and thereby providing wearer comfort for the patient. In one embodiment, the carrier is in the form of a waist pouch. In another embodiment, the carrier is in the form of a waist pouch and having at least one strap running across the shoulder of the patient. In another embodiment, the carrier is in the form of a knapsack (backpack) that can be worn at the back with two straps running across each shoulder of the patient. Advantageously, the carrier may also be aesthetically designed for wearable active lifestyle and can be used as a desktop device.

BRIEF DESCRIPTION OF DRAWINGS

The accompanying drawings illustrate disclosed embodiments and serve to explain the principles of the disclosed embodiments. It is to be understood, however, that the drawings are designed for purposes of illustration only, and not as a definition of the limits of the invention.

DETAILED DESCRIPTION

Figure 1A:
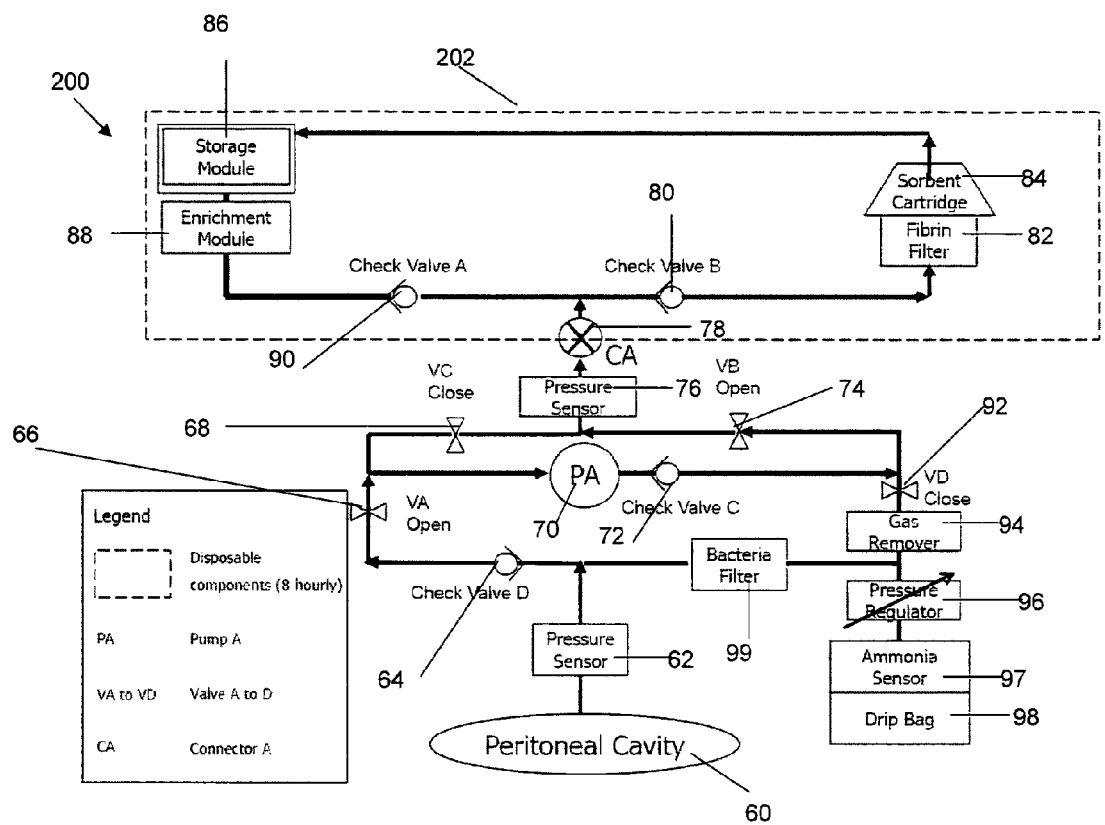
FIG. 1a is a schematic of one embodiment of the disclosed flow system, wherein the flow of the dialysate is toward the sorbent from the peritoneal cavity.

Referring now to FIG. 1a, there is shown one embodiment of the disclosed flow system (200), wherein the flow of the dialysate is toward the sorbent (84) from the peritoneal cavity (60). The dialysate is first drawn out of the peritoneal cavity (84) and passes through a pressure sensor (62) to determine if the pressure of the dialysate being withdrawn from the peritoneal cavity (60) is within a safe limit.

Valve check point one (64) ensures that valve D (92) is closed before the flow of the dialysate is allowed to proceed. Once valve check point one (64) indicates that valve D (92) is closed, the dialysate is pumped by pump A (70) through valve A (66). The dialysate then flows to valve check point two (72), which determines whether valve c (68) is closed. If affirmative, the dialysate is allowed to proceed across valve B (74) towards a pressure sensor (76). The pressure sensor (76) determines if the dialysate flow is at the correct pressure before allowing the dialysate to proceed into the next flow circuit (202) comprising the sorbent (84) via connector A (78).

In the flow circuit (202) comprising the sorbent (84), the dialysate flow past valve check point three (80), which determines if valve B (74) is closed as part of the flow feedback system ensures the dialysate can be returned back to the peritoneal cavity (60) via the right path. The dialysate then continues to flow through a fibrin filter (82) to remove any residual fibrin that may cause, damage to the sorbent (84). After removal of residual fibrin, the dialysate passes through the sorbent (84) for the removal of urea and other unwanted ions as described above. The regenerated dialysate exiting from the sorbent (84) flows towards a storage module (86) for the temporary storage of excess dialysate. After which, the dialysate flows past an enrichment module (88), which optionally dispenses a predetermined amount of desired substance, such as hormones, nutrients etc, into the dialysate before the dialysate is returned back to the peritoneal cavity (60). Valve check point four (90) is present near the exit of the enrichment module to determine if valve A (66) is closed as part of the flow system's feedback control to ensure the dialysate is returned back to the peritoneal cavity (60) via the right path.

Figure 1B:
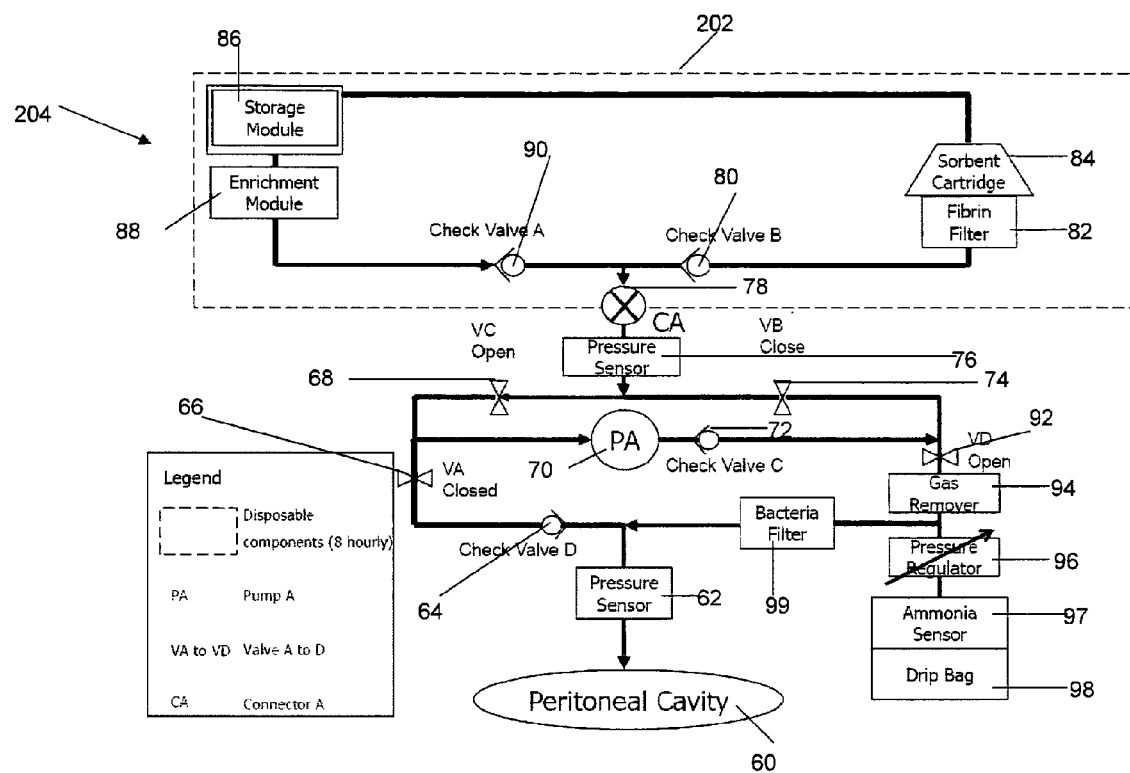
FIG. 1b is a schematic of one embodiment of the disclosed flow system, wherein the flow of the dialysate is from the enrichment module to the peritoneal cavity.

Referring now to FIG. 1b there is shown a schematic diagram of one embodiment of the disclosed flow system (204), wherein the flow of the dialysate is from the enrichment module (88) to the peritoneal cavity (60). As the dialysate exits from the enrichment module (88), it passes valve check point four (90) which determines of valve A (66) is now closed. If positive, the dialysate is allowed to flow through connector A (78) past the pressure sensor (76) which again determines if the pressure of the dialysate flow is in the correct region for entry into the peritoneal cavity (60). The dialysate then flows through valve C (72) which is now open, towards pump A (70). Pump A (70) provides the driving force for delivering the dialysate back to the peritoneal cavity (60). Pump A (70) propels the dialysate to a gas remover (94) through valve D (92) to remove any unwanted gas emitted during the dialysis operation. A small volume of dialysate is shunted to a pressure regulator (96), which receives feedback from the pressure sensor and adjusts the pressure of the dialysate flow accordingly by changing the propelling power of pump A (70). The small volume of dialysate is then allowed to enter an ammonia sensor (97) to determine of the ammonia level in the dialysate is within a safe range. After detection, this small volume of dialysate is then collected in a drip bag (98) to be discarded. The majority of the dialysate flows from the gas remover (94) to a bacterial filter (99) for removal of bacteria from the dialysate before returning the dialysate back to the peritoneal cavity (60).

Figure 2A:
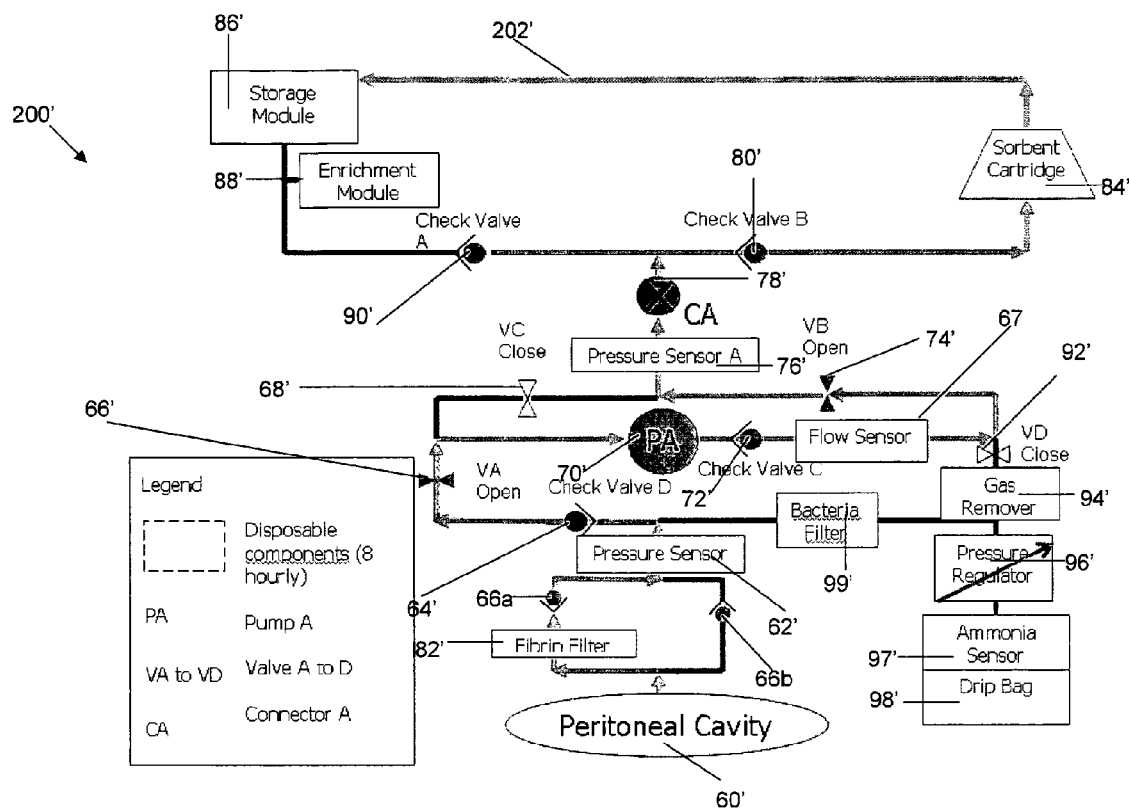
FIG. 2a is a schematic of the flow system in an alternate arrangement, wherein the flow of the dialysate is toward the sorbent from the peritoneal cavity.

Referring to FIG. 2a there is shown the flow system (200') in an alternative arrangement with the fibrin filter (82') located near the outlet of the peritoneal cavity (60'), wherein the flow of the dialysate is toward the sorbent (84') from the peritoneal cavity (60'), i.e. outflow mode. A number of technical features that are the same as that shown in FIG. 1a described above are indicated by the same reference numeral but with a prime symbol ('). Valve A (66') and B (74') open while Valve C (68') and D (92') close. A tidal volume (prescribed by clinician) of dialysate is pumped from the patient's peritoneal cavity (60') into the storage module (86') via the fibrin filter (82'), pressure sensor B (62'), pump (70'), flow sensor (67), pressure sensor A (76') and sorbent (84'). During this mode the flow rate is controlled by the speed of the pump (70') and is maintained at constant rate as determined by the clinician. When the flow sensor (67) sensed that a volume of dialysate equal to the tidal volume has been pumped into the storage module (86), the system enters the inflow mode as depicted in FIG. 2b.

It is possible that during the outflow mode, particularly when the patient is in bed, the tube connecting the patient's peritoneal cavity (60') to the. system may be choked. Under such circumstances the peritoneal pressure sensor (62') detects an abnormal pressure and the system triggers an audio-visual alarm that is cleared only when the situation is back to normal again. Audible alarm can be muted by a "Mute" button located on a pressure sensor (62') for a short period of time that is programmable.

Figure 2B:
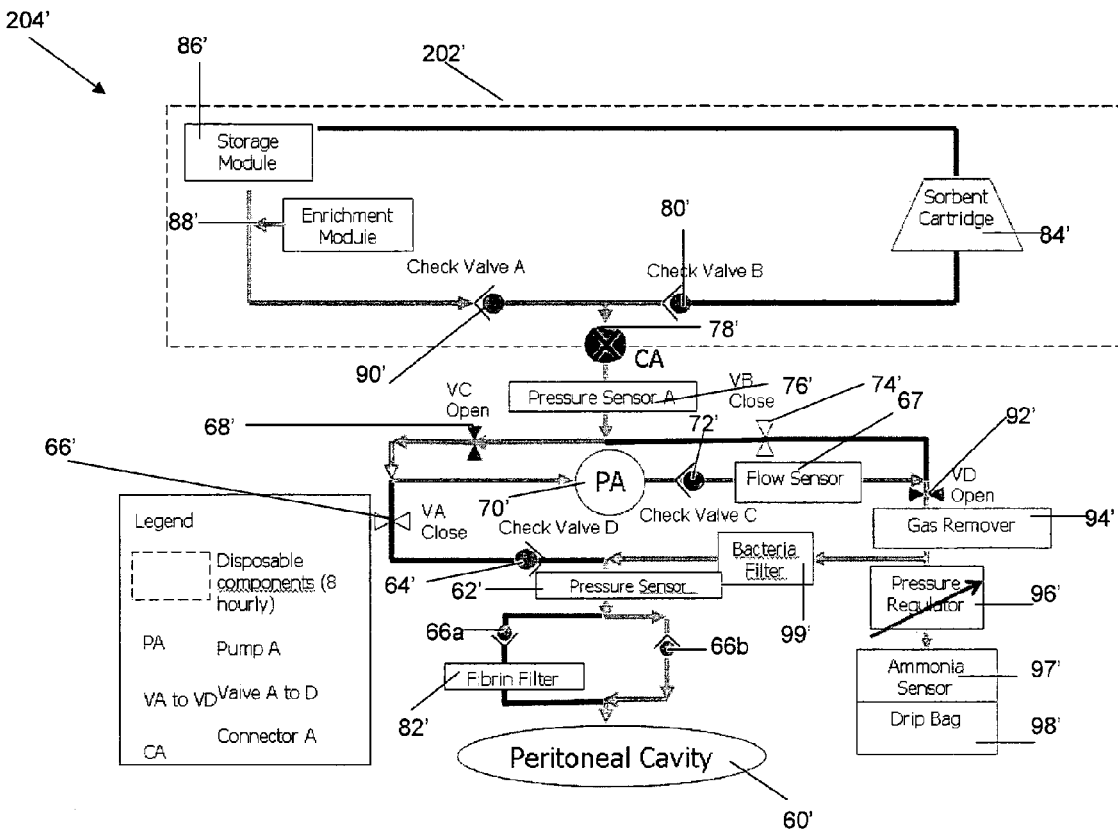
FIG. 2b is a schematic of the flow system in an alternate arrangement, wherein the flow of the dialysate is from the enrichment module to the peritoneal cavity.

Referring to FIG. 2b there is shown the flow system (204') in an alternative arrangement with the fibrin filter (82') located near the outlet of the peritoneal cavity (60'), wherein the flow of the dialysate is from the enrichment module (88') to the peritoneal cavity (60'), i.e. inflow mode. A number of technical features that are the same as that shown in FIG. 1b described above are indicated by the same reference numeral but with a prime symbol ('). Valve C (68') and D (92') open while Valve A (90') and B (80') close. The dialysate contained in the storage module (86') is pumped back to the patient's peritoneal cavity (60') via the pressure sensor A (76'), flow sensor (67), gas remover (94') and the bacteria filter (99'), pressure sensor B (62') and back to the peritoneal cavity (60'). During this mode the flow rate is controlled by the speed of the pump (70') and is maintained at constant rate as determined by the clinician. When the storage module (86') pressure sensor sensed an abnormal pressure that signals that the storage module (86') is empty, the system returns to the outflow mode as shown in FIG. 2a.

It is possible that during the outflow mode, particularly when the patient is in bed, the tube connecting the patient's peritoneal cavity (60') to the system may be choked. Under such circumstances the peritoneal pressure sensor (62') detects an abnormal pressure and the system triggers an audio-visual alarm that is cleared only when the situation is back to normal again. Audible alarm can be muted by the "Mute" button located on the pressure sensor (62') for a short period of time that is programmable.

During the inflow mode the system (204') pumps a small amount of dialysate through the ammonia sensor (97'). The presence of ammonia in the dialysate will cause the system (204') to stop automatically after the storage module (86') is empty and triggers an audio-visual alarm to prompt the patient to change the sorbent (84'). The alarm will be cleared automatically when the ammonia sensor (97') does not detect anymore ammonia in the dialysate. Audible alarm can be muted by the "Mute" button located on the ammonia sensor (97') for a short period of time that is programmable.

The system also keeps track of the time that the present sorbent (84') is in use. When the sorbent (84') is in use for more than the predetermined lifespan, an audio-visual alarm is triggered to prompt the patient to change the sorbent (84'). The alarm will be cleared automatically after power down. Audible alarm can be muted by the "Mute" button for a short period of time that is programmable.

Figure 3A:
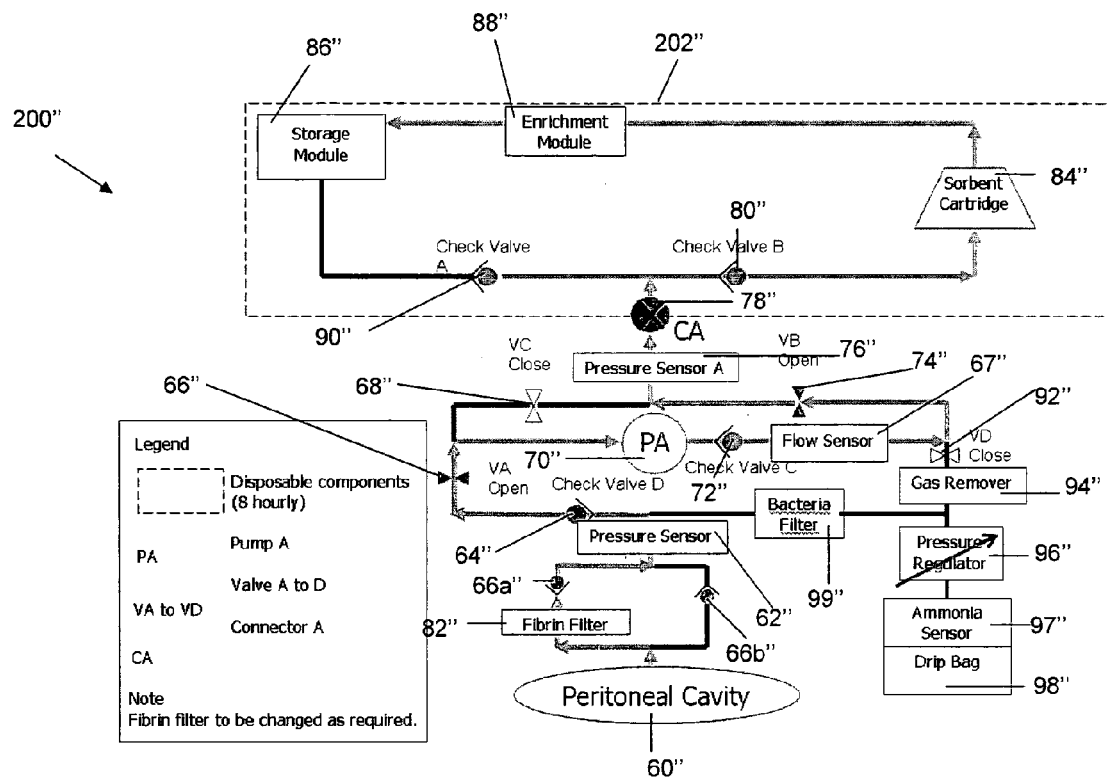
FIG. 3a is a schematic of the flow system in yet another alternate arrangement, wherein the flow of the dialysate is toward the sorbent from the peritoneal cavity.

Referring to FIG. 3a there is shown the flow system (200") in yet another alternative arrangement with the enrichment module (88") located between the sorbent (84") and the storage module (86"), wherein the flow of the dialysate is toward the sorbent (84") from the peritoneal cavity (60"), i.e. outflow mode. A number of technical features that are the same as that shown in FIG. 2a described above are indicated by the same reference numeral but with prime symbols ("). The operation of the flow system (200") in the outflow mode as depicted in FIG. 3a is similar to that described above for FIG. 2a.

Figure 3B:
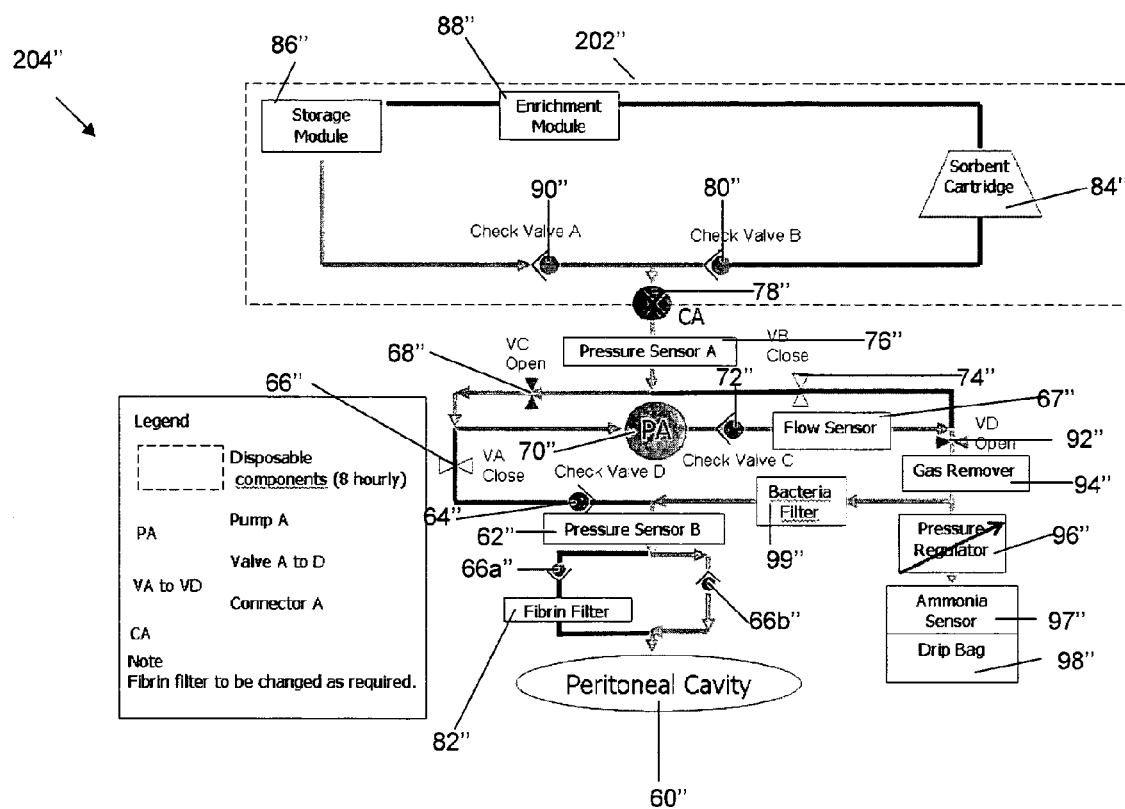
FIG. 3b is a schematic of the flow system in yet another alternate arrangement, wherein the flow of the dialysate is from the enrichment module to the peritoneal cavity.

Referring to FIG. 3b there is shown the flow system (204") in yet another alternative arrangement with the enrichment module (88") located between the sorbent (84") and the storage module (86"), wherein the flow of the dialysate is from the enrichment module (88") to the peritoneal cavity (60"), i.e. inflow mode. A number of technical features that are the same as that shown in FIG. 2b described above are indicated by the same reference numeral but with prime symbols ("). The operation of the flow system (200") in the inflow mode as depicted in FIG. 3b is similar to that described above for FIG. 2b.

Figure 4:
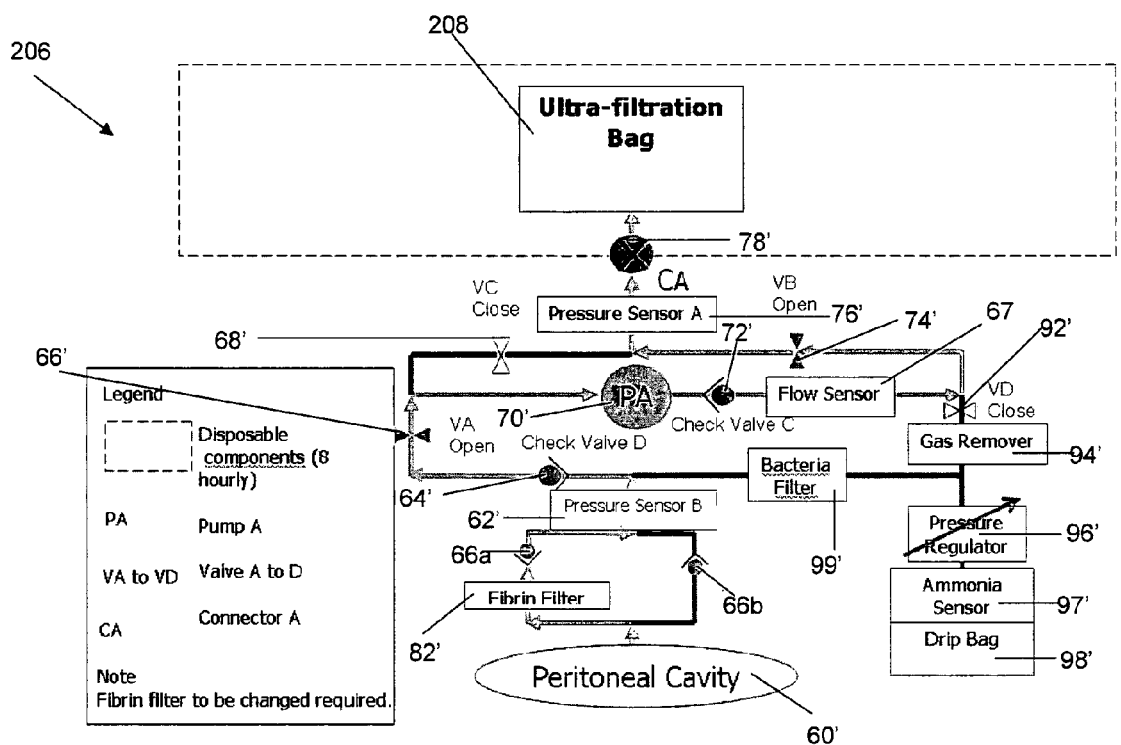
FIG. 4 is a schematic of the flow circuit for the removal of the ultrafiltrate as disclosed herein.

Referring now to FIG. 4 there is shown a schematic of the flow circuit (206) for the removal of the ultrafiltrate as disclosed herein, i.e. ultrafiltration removal mode. A number of technical features that are the same as that described above are indicated by the same reference numeral but with a prime symbol (').

During the ultrafiltration mode the entire volume of dialysate including the amount of ultrafiltrate generated by the patient is pump out of the patient's peritoneal cavity (60') and into an ultrafiltration bag (208). When the peritoneal pressure sensor B (62') sensed an abnormal pressure signaling that the peritoneal cavity (60') is empty, a volume of the dialysate equal to the original total volume as prescribed by the clinician is then pump back into the patient's peritoneal cavity (60'). The remaining volume in the ultrafiltration bag (208) is the ultrafiltrate and is discarded. This amount is determined by subtracting the volume pumped into the patient's peritoneal cavity (60') from the volume pumped out of the peritoneal cavity (60') and recorded in the Secure Digital (SD) card for clinical assessment by the clinician.

During operation the patient can Start/Stop the pump (70') any number of times by pressing the Start/Stop button located thereon so long as the sorbent (not shown) is not in use continuously for more than its lifespan. The parameters measured during the operation are logged into the SD card for clinical assessment by the clinician.

Figure 5A:
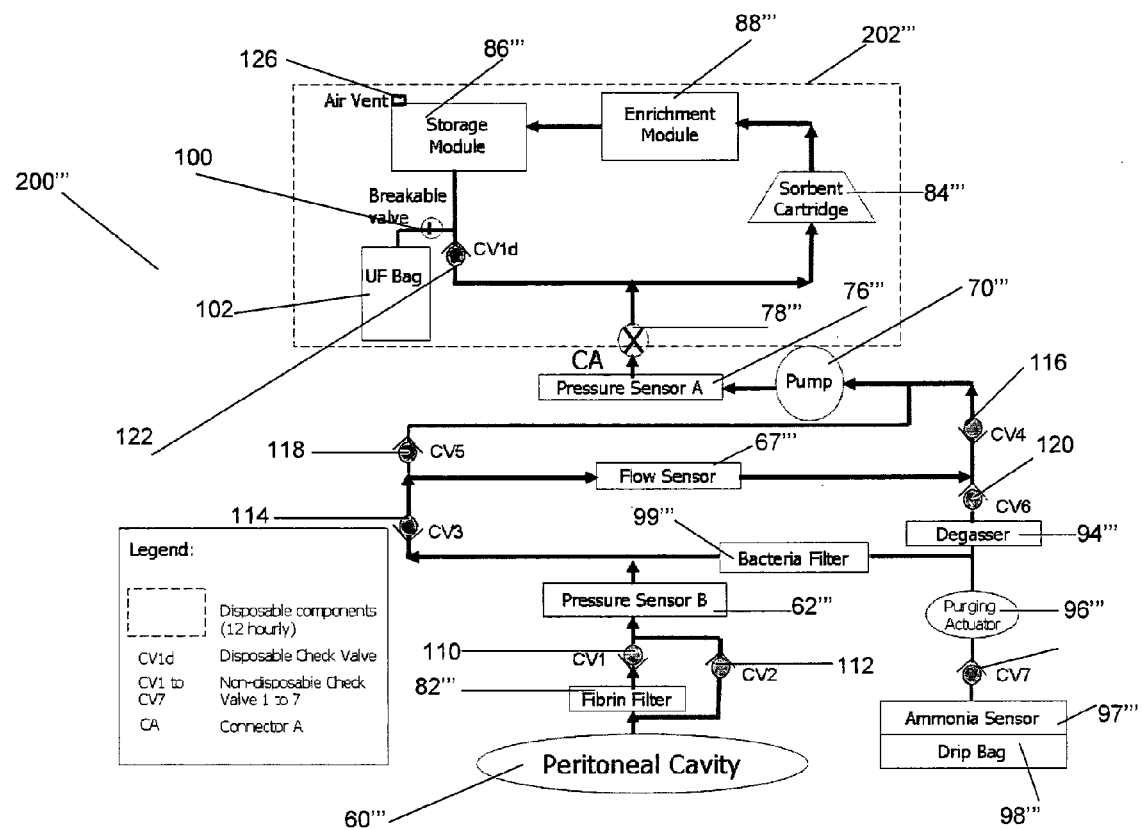
FIG. 5a is a schematic of the flow system in yet another alternate arrangement with a number of check valves within the flow system, wherein the flow of the dialysate is toward the sorbent from the peritoneal cavity.

Referring to FIG. 5a there is shown the flow system (200''') in yet another alternative arrangement with a number of check valves (110, 112, 114, 116, 118, 120, 122 and 124) within the flow system, wherein the flow of the dialysate is toward the sorbent (84''') from the peritoneal cavity (60'''), i.e. outflow mode. A number of technical features that are the same as that shown in FIG. 3a described above are indicated by the same reference numeral but with prime symbols ('''). The operation of the flow system (200''') in the outflow mode as depicted in FIG. 5a is similar to that described above for FIG. 3a, with the exception that in this configuration, the valves check points (operated by a valve actuating motors) described in FIG. 3a are replaced by a number of check valves (110, 112, 114, 116, 118, 120, 122 and-124). The check valves allow the flow system to be implemented in a much simpler manner. FIG. 5a also shows an additional air vent (126) present on the storage module to release pent up gases, a breakable valve 100 leading to an ultrafiltration bag (102).

Figure 5B:
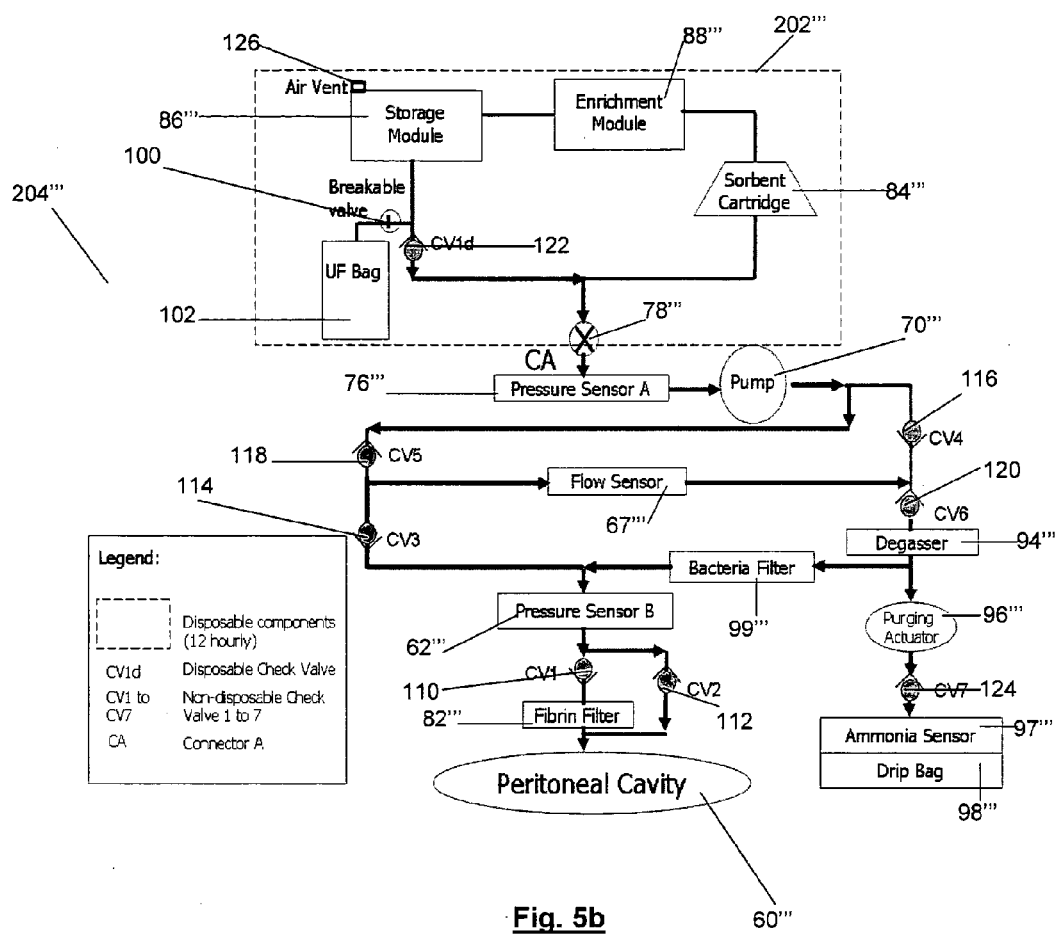
FIG. 5b is a schematic of the flow system in yet another alternate arrangement with a number of check valves within the flow system, wherein the flow of the dialysate is from the enrichment module to the peritoneal cavity.

Referring to FIG. 5b there is shown the flow system (204''') in yet another alternative arrangement with a number of check valves (110, 112, 114, 116, 118, 120, 122 and 124) within the flow system, wherein the flow of the dialysate is from the enrichment module (88') to the peritoneal cavity (60'), i.e. inflow mode. A number of technical features that are the same as that shown in FIG. 3b described above are indicated by the same reference numeral but with prime symbols ('''). The operation of the flow system (200''') in the inflow mode as depicted in FIG. 5b is similar to that described above for FIG. 3b with the exception that in this configuration, the valves check points (operated by a valve actuating motors) described in FIG. 3a are replaced by a number of check valves (110, 112, 114, 116, 118, 120, 122 and 124). The check valves allow the flow system to be implemented in a much simpler manner. FIG. 5b also shows an additional air vent (126) present on the storage module to release pent up gases, a breakable valve 100 leading to an ultrafiltration bag (102).

Figure 5C:
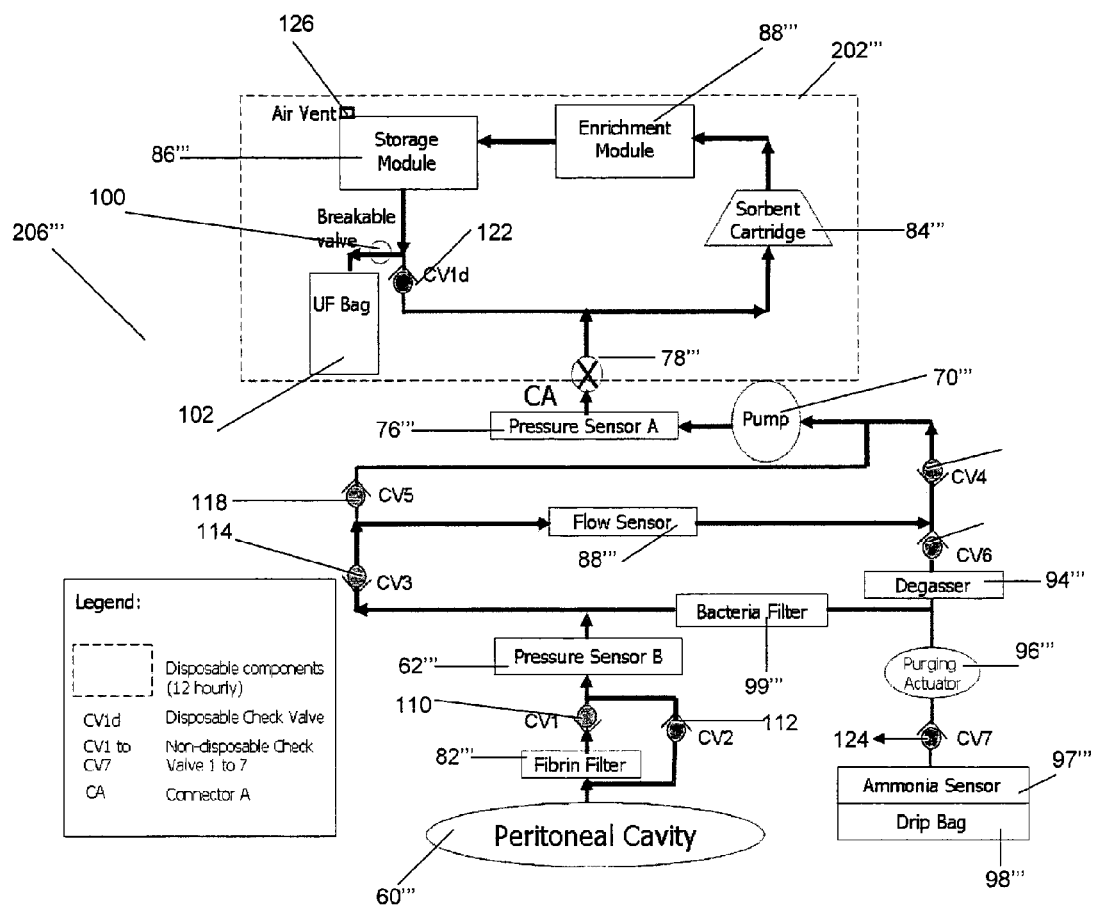
FIG. 5c is a schematic of the flow system for the removal of the ultrafiltrate as disclosed herein in an alternative configuration from that shown in FIG. 4.

Referring to FIG. 5c there is shown the flow system (206''') for the removal of the ultrafiltrate as disclosed herein, i.e. ultrafiltration mode in an alternative configuration from that shown in FIG. 4. A number of technical features that are the same as that shown in FIG. 4 described above are indicated by the same reference numeral but with prime symbols ('''). The operation of the flow system (200''') in the ultrafiltration mode as depicted in FIG. 5c is similar to that described above for FIG. 4 with the exception that in this configuration, the valves check points (operated by a valve actuating motors) described in FIG. 3a are replaced by a number of check valves (110, 112, 114, 116, 118, 120, 122 and 124). The check valves allow the flow system to be implemented in a much simpler manner. FIG. 5c also shows an additional air vent (126) present on the storage module to release pent up gases, a breakable valve 100 leading to an ultrafiltration bag (102).

Figure 6:
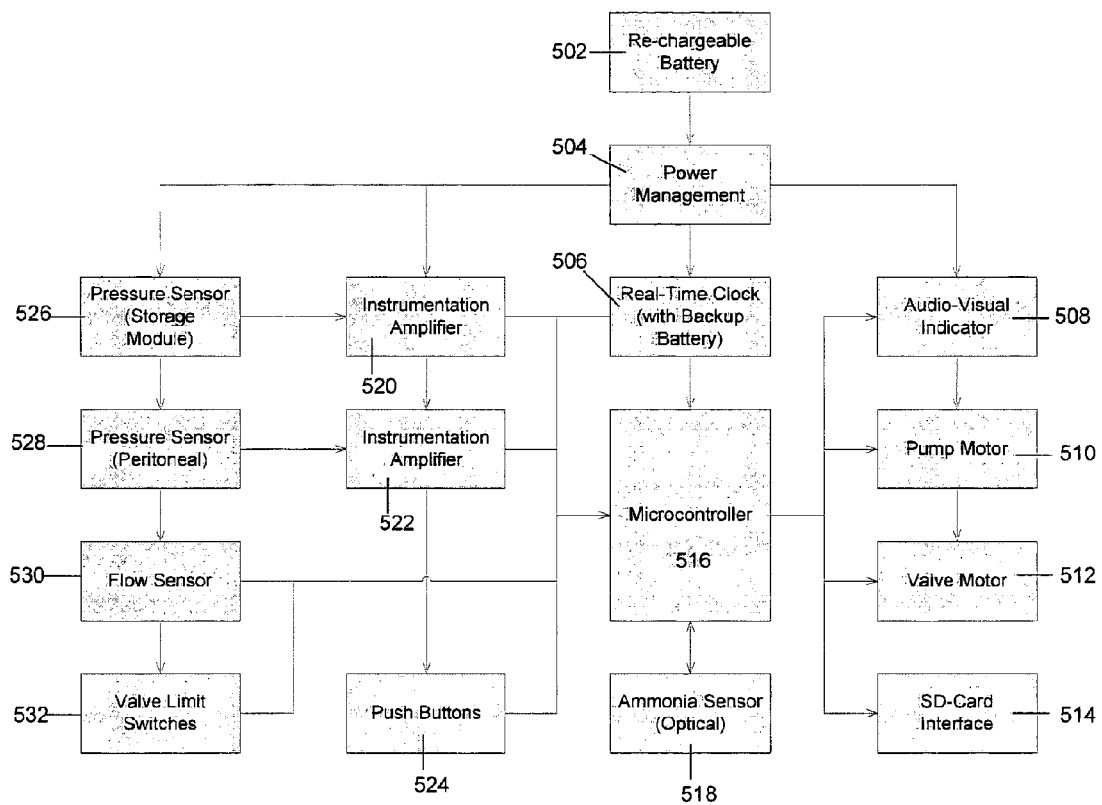
FIG. 6 is a functional block diagram of the control system of the flow system disclosed herein.

Referring now to FIG. 6 there is shown a functional block diagram of the control system (500) of one embodiment of the flow system disclosed herein. The control system (500) of the flow system is powered by a rechargeable battery (502). Electrical access to the rechargeable battery (502) by the flow system, is determined by the power management module (504) which comprises a on/off switch (not shown). The power management module (504) also allows the rechargeable battery to power a Real-Time Clock (506) which itself comprises a backup battery in case of failure of the Rechargeable battery (502). The control system (500) further comprises a microcontroller (516) which is preprogrammed to receive and send signals to the various components of the control system and the flow system. The microcontroller is electrically linked to an ammonia sensor (518), audio visual indicator (508), pump motor (510), valve motor (512), Secure Digital (SD) card interface (514), Instrumentation Amplifier (520,522), push buttons (524), pressure sensors (526, 528), flow sensor (530) and valve limit switches (532).

When in use, the flow system is first powered up by the turn-on switch on the Power management module (504). When the turn-on switch is pressed, the power management module (506) allows power access of the microcontroller (516) and other components of the control system, flow system and dialysis device, leading to the activation of the entire dialysis device. The pump motor (510) and valve motor (512) are activated to drive the dialysis fluid from the peritoneal cavity of the patient into the dialysis device. The pressure sensor (528) senses the pressure of the peritoneal cavity to determine if any obstructions had occurred between the peritoneal cavity and the pump. A signal is then sent from the pressure sensor (528) to the instrument amplifier (522), which amplifies the signal and passes the amplified signal to the microcontroller (516). Similarly, the pressure sensor (526) senses the pressure of the storage module to determine if any obstructions had occurred between the peritoneal cavity and the pump, before transmitting the signal via the instrument amplifier (520) to the microcontroller (516). From the amplified signals obtained from the pressure sensors (526,528), the microcontroller (516) then decides whether to activate the audio visual indicator (508) to alert the user of any obstructions. Feedback signals are also received by the microcontroller (516) from the flow sensor (530) and the valve limit switches (532). From the feedback signals obtained by the flow sensor (530) and the valve limit switches (532), the microcontroller (516) decides if the direction of flow is correct and proceeds to activate the valve motor (512), which in turn controls the opening and closing of the various valves in the system to ensure that the dialyate flow is in the correct direction. The control system is also programmed to sound off the audio-visual indicator (508) after 6 hours of usage and 6 hours 45 minutes of usage as a reminder to the user to replace the spent sorbent. The time of usage is actively monitored by the Real Time Clock (506). The SD-card interface (514) stores the patient's specific requirements and saves a log of the events that have occurred during the operation of the flow system as a reference for the clinician.

Figure 7:
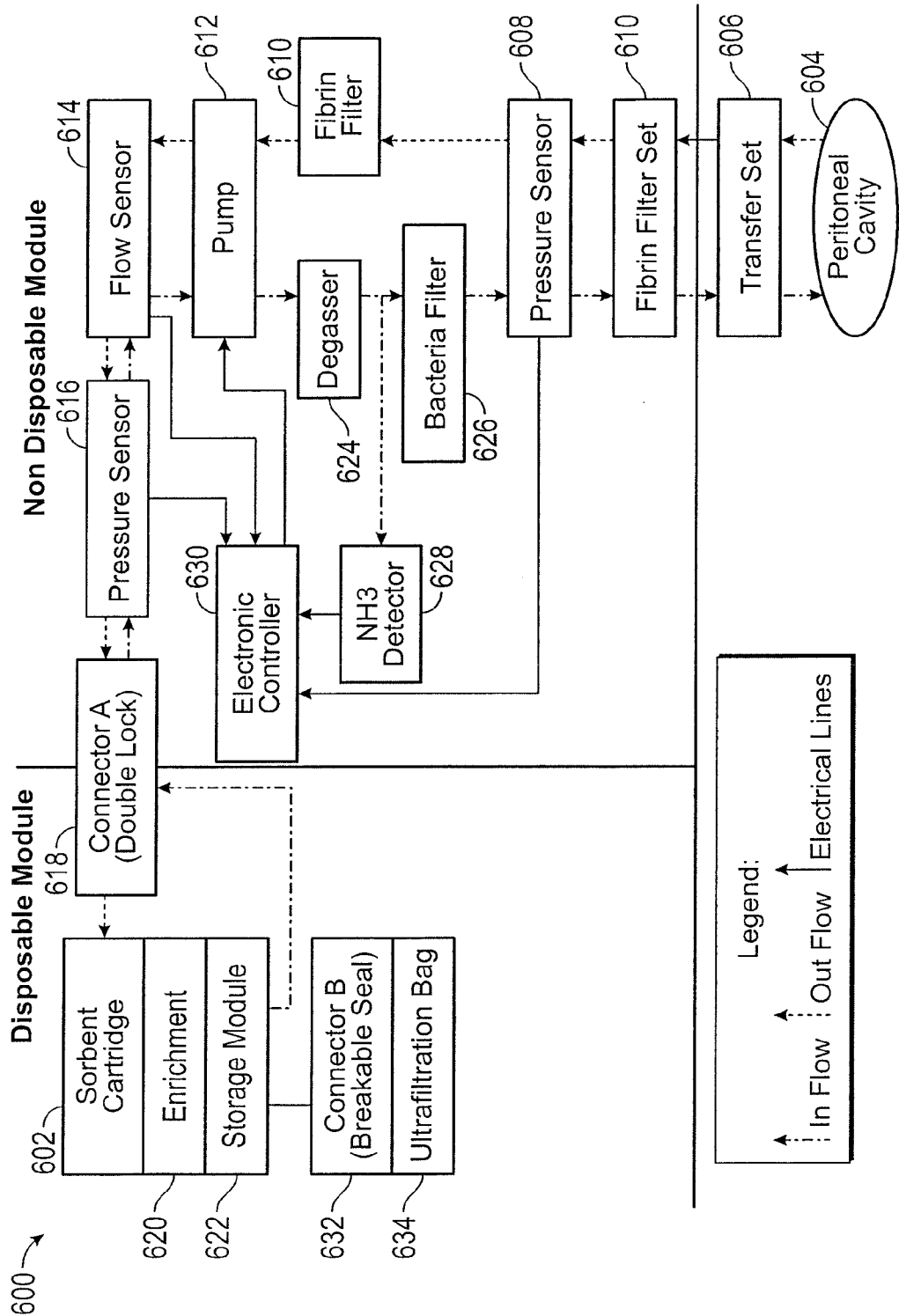
FIG. 7, is a flow chart showing the flow of dialyate in an embodiment of the flow system.

Referring now to FIG. 7, there is shown a flow chart showing the flow of dialysate in an embodiment of the flow system (600), wherein the flow of the dialysate is toward the sorbent (602) from the peritoneal cavity (604) as indicated by the upward arrow. The dialysate is first drawn out of the peritoneal cavity (604) and passes through a transfer set (606) and pressure sensor (608) to determine if the pressure of the dialysate being withdrawn from the peritoneal cavity (604) is within a safe limit.

The dialysate flows through a fibrin filter (610) to remove any residual fibrin that may cause damage to the flow system (600). After removal of residual fibrin, the dialysate passes through the Pump (612), flow sensor 614 and another pressure sensor (616). The dialysate then passes through Connector A (618) and proceeds on to the sorbent (602). The dialysate passes through the sorbent (602) for the removal of urea and other unwanted ions as described above. The regenerated dialysate exiting from the sorbent (602) flows towards the Enrichment Module (620) which dispenses a predetermined amount of desired substance, such as hormones, nutrients, antibiotics, etc, into the dialysate before the dialysate reaches the storage module (622) for the temporary storage of excess dialysate.

A tidal volume (prescribed by clinician) of dialysate is pumped from the patient's peritoneal cavity (604) into the storage module (622). During this outflow mode the flow rate is controlled by the speed of the pump (612) and is maintained at constant rate as determined by the clinician. When the flow sensor (614) sensed that a volume of dialysate equal to the tidal volume has been pumped into the storage module (622), the system enters the inflow mode wherein the flow of the dialysate is from the storage module (622) to the peritoneal cavity (604).

It is possible that during the outflow mode, particularly when the patient is in bed, the tube connecting the patient's peritoneal cavity (604) to the system may be choked. Under such circumstances the pressure sensor (616) nearer to the transfer set (606) detects an abnormal pressure and the system triggers an audio-visual alarm that is cleared only when the situation is back to normal again. Audible alarm can be muted by a "Mute" button for a short period of time that is programmable.

FIG. 7 also shows the flow of the dialysate is from the storage module (622) to the peritoneal cavity (604) as indicated by the direction of the arrow originating from the storage module. As the dialysate exits from the storage module (622), it passes Connector A (618) and proceeds on to the pressure sensor (616), flow sensor (614) and Pump (612), The dialysate is then diverted to a degasser (624). Before the dialysate is allowed to proceed on to a bacteria filter (626) from the degasser (624), a small volume of dialysate will be purged from the flow system (600) to an ammonia sensor (628) for the detection of ammonia in the dialysate. The ammonia level in the dialysate is then determined if it is within a safe range. And the majority of the dialysate flows from the degasser (624) to a bacteria filter (626) for removal of bacteria. The dialysate now flows from the bacteria filter (626) to pressure sensor (608), fibrin filter set (610) and transfer set (606) and back to the peritoneal cavity (604). During this mode the flow rate is controlled by the speed of the pump (612) and is maintained at constant rate as determined by the clinician. When pressure sensor (616) nearer to the connector (618) sensed an abnormal pressure that signals that the storage module (622) is empty, the system returns to the outflow mode from the peritoneal cavity (604) to the sorbent (622).

It is possible that during the inflow mode, particularly when the patient is in bed, the tube connecting the patient's peritoneal cavity (604) to the system may be choked. Under such circumstances the pressure sensor (608) nearer to the fibrin filter set (610) detects an abnormal pressure and the system triggers an audio-visual alarm that is cleared only when the situation is back to normal again. An audible alarm can be muted by a "Mute" button for a short period of time that is programmable.

During the inflow mode, the flow system (600) diverts a small volume of dialysate through the ammonia sensor (628). The presence of ammonia in the dialysate will cause the flow system (600) to stop automatically after the storage module (622) is empty and triggers an audio-visual alarm to prompt the patient to change the sorbent (602). The alarm will be cleared automatically when the ammonia sensor (628) does not detect anymore ammonia in the dialysate. Audible alarm can be muted by the "Mute" button for a short period of time that is programmable.

The system also keeps track of the time that the present sorbent (602) is in use. When the sorbent (602) is in use for more than the predetermined lifespan, an audio-visual alarm is triggered to prompt the patient to change the sorbent (602). The alarm will be cleared automatically after power down.

Audible alarm can be muted by the "Mute" button for. a short period of time that is programmable.

After the audio-visual alarm to change the sorbent is activated, the patient will stop the dialysis mode and activate the ultrafiltration mode of operation after breaking the seal in Connector B. This allows the entire volume of dialysate to be pumped from the peritoneal cavity into the ultrafiltration bag. When the peritoneal cavity is empty prompted by an abnormal negative pressure at the pressure sensor near to the transfer set, the system will return an amount of dialysate equal to the sum of tidal plus reserve volume (as determined by the clinician) into the patient's peritoneal cavity. The remaining amount of dialysate in the ultrafiltration bag is the total ultrafiltration that the patient generated minus the amount of dialysate in the sorbent after exhaustion.

Upon completion of the ultrafiltration mode, the system is shut down and the disposal module is disconnected from the non disposal module and replace with a new disposal module. After which the rechargeable battery is replaced with a new rechargeable battery.

Figure 8A:
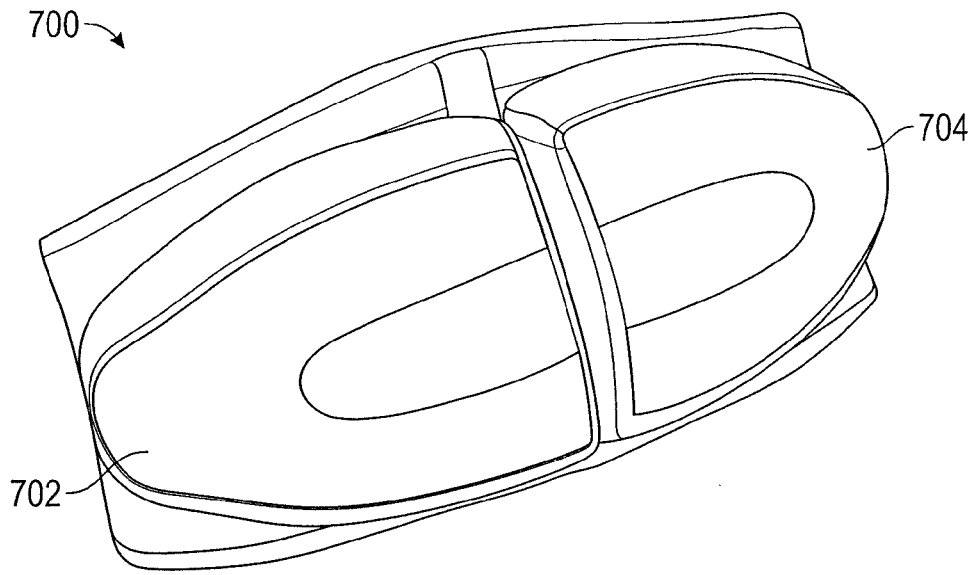
FIG. 8a-8c are pictures of one embodiment of the carrier for the dialysis device/flow system disclosed herein.
Figure 8B:
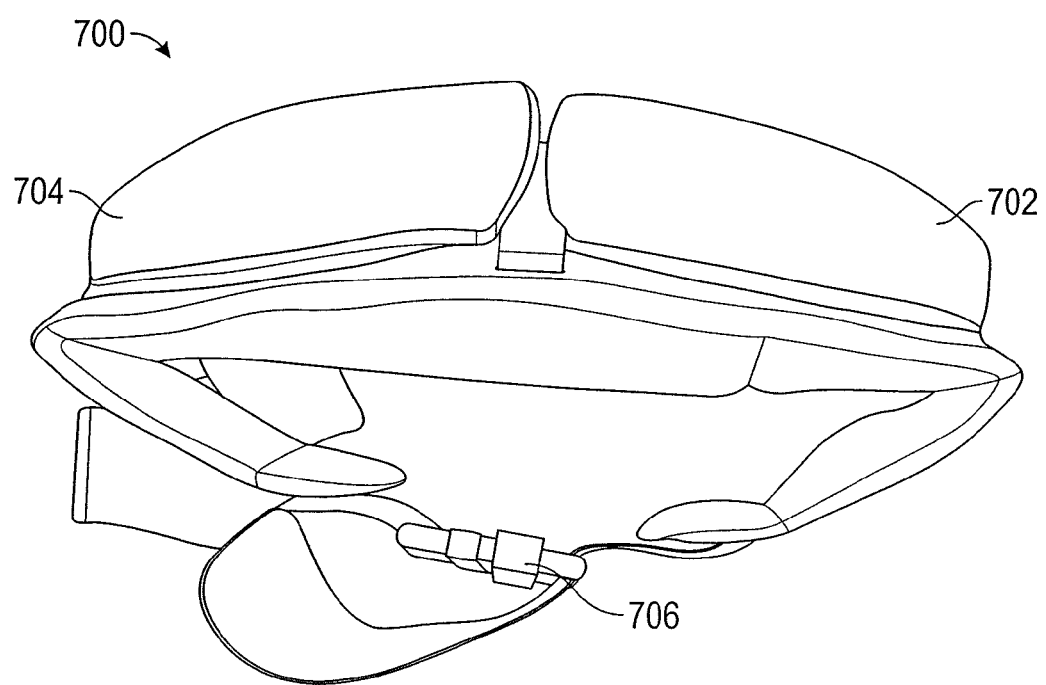
Figure 8C:
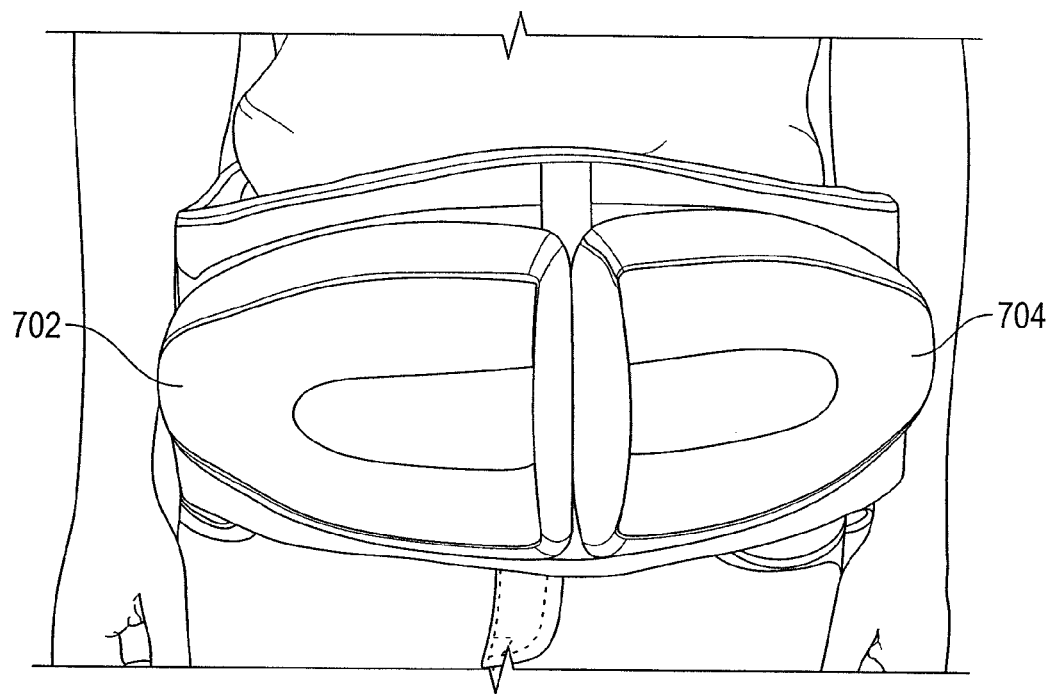

Referring now to FIG. 8a-8c, there is shown one embodiment of the carrier (700) for the dialysis device/flow system. The dialysis device/flow system is attached to a belt like carrier (300) that can be worn around the waist of the user. One compartment (702) is capable of storing the disposable module while another compartment (704) is capable of storing the non-disposable part of the dialysis device/flow. system. The carrier (700) is attached to a buckle (706) for securing the carrier to the user.

Figure 9A:
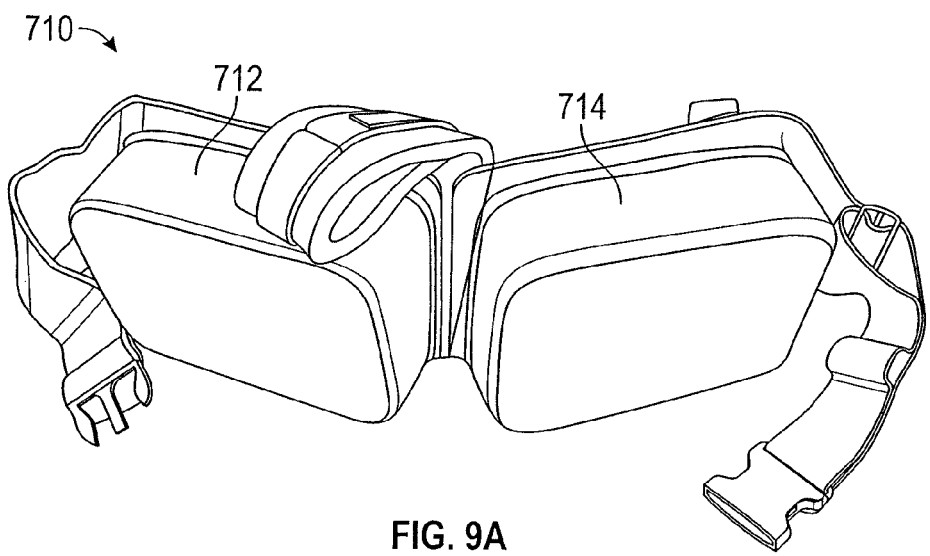
FIG. 9a-9c are pictures of another embodiment of the carrier for the dialysis device/flow system disclosed herein.
Figure 9B:
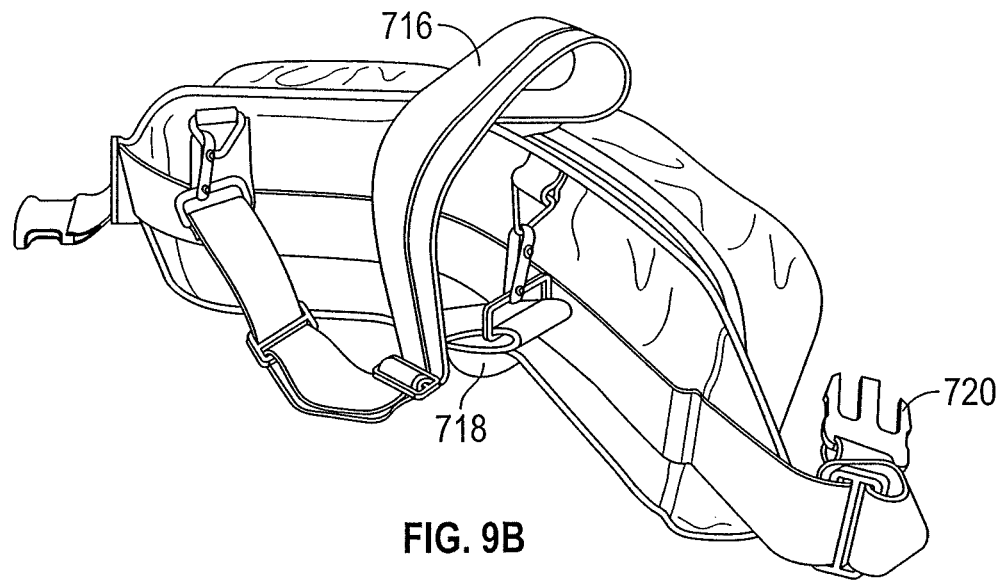
Figure 9C:
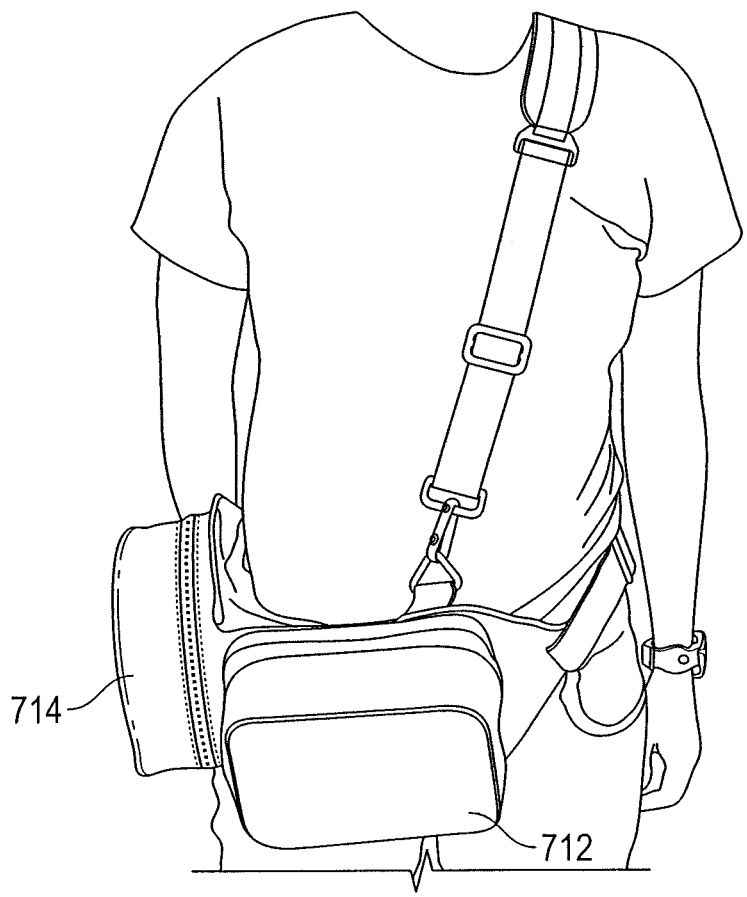

Referring to FIG. 9a-9c, pictures of another embodiment of the carrier in the form of a sling pouch (710) for the dialysis device/flow system are shown. The dialysis device/flow system is attached to a carrier (710) that can be slung across the shoulder of the user. One compartment (712) is capable of storing the disposable module while another compartment (714) is capable of storing the non-disposable part of the dialysis device/flow system. The transfer set and fibrin filter set is located at the back of the carrier (718). The carrier (700) is attached to a buckle (706) for securing the carrier to the user and a comfort sling (716) for slinging across the user's shoulder.

Figure 10A:
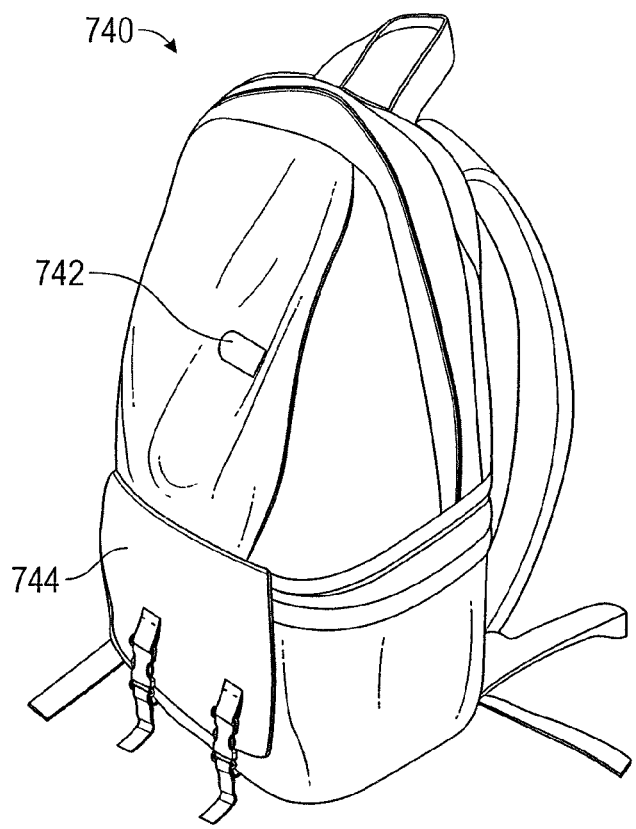
FIG. 10a-10c are pictures of yet another embodiment of the carrier for the dialysis device/flow system disclosed herein.
Figure 10B:
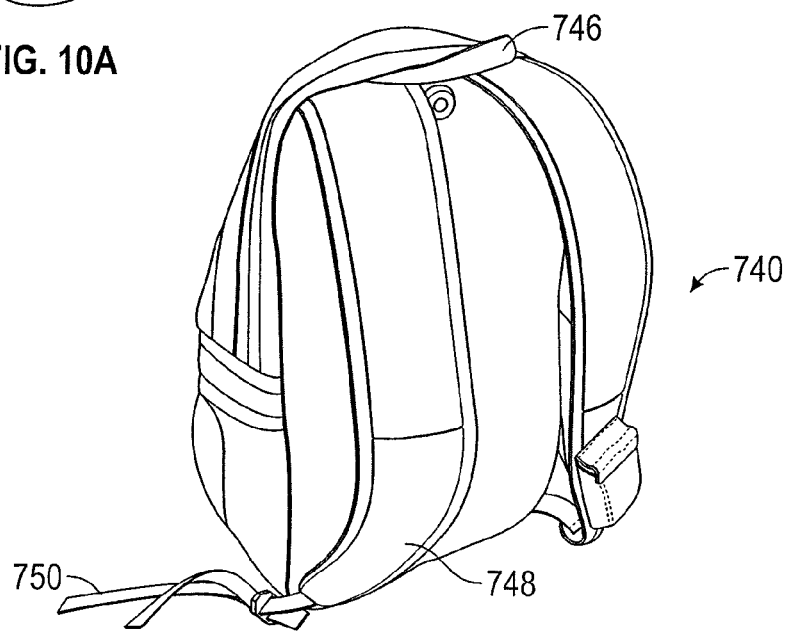
Figure 10C:
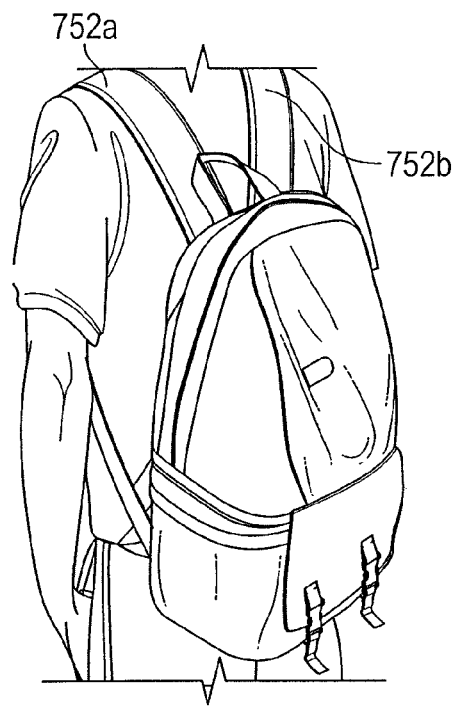

Referring to FIG. 10a-10c, pictures of another embodiment of the carrier in the form of a backpack (740) for the dialysis device/flow system are shown. The dialysis device/flow system is attached to a backpack like carrier (740) having straps (752a and 752b) that runs over the users shoulder. The straps (752a and 752b) support the entire dialysis device/flow system and distribute the weight of the dialysis device/flow system across both shoulders of the patient. One compartment (744) is capable of storing the disposable module while another compartment (742) is capable of storing the non-disposable part of the dialysis device/flow system. The transfer set and fibrin filter set is located at the back of the carrier (748). The carrier (740) is attached to a buckle (750) for securing the carrier to the user.

Figure 11:
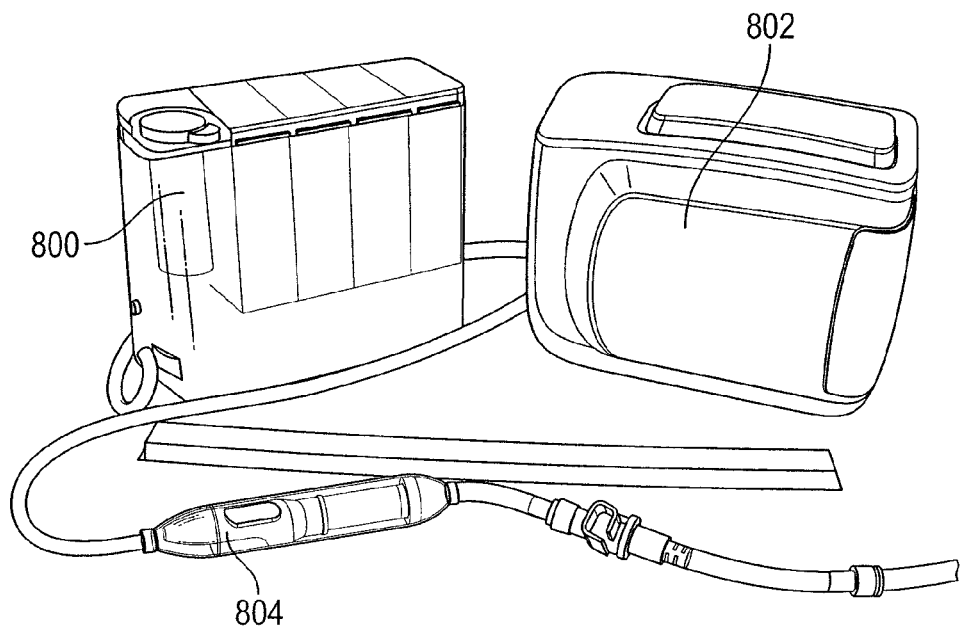
FIG. 11 is a picture of a prototype of one embodiment of the entire flow system disclosed herein.

Referring now to FIG. 11, there is shown a picture of a prototype of one embodiment of the entire flow system disclosed herein, with a disposable module (800), the non-disposable component of the flow system (802) and the transfer set (804) described above.

Figure 12:
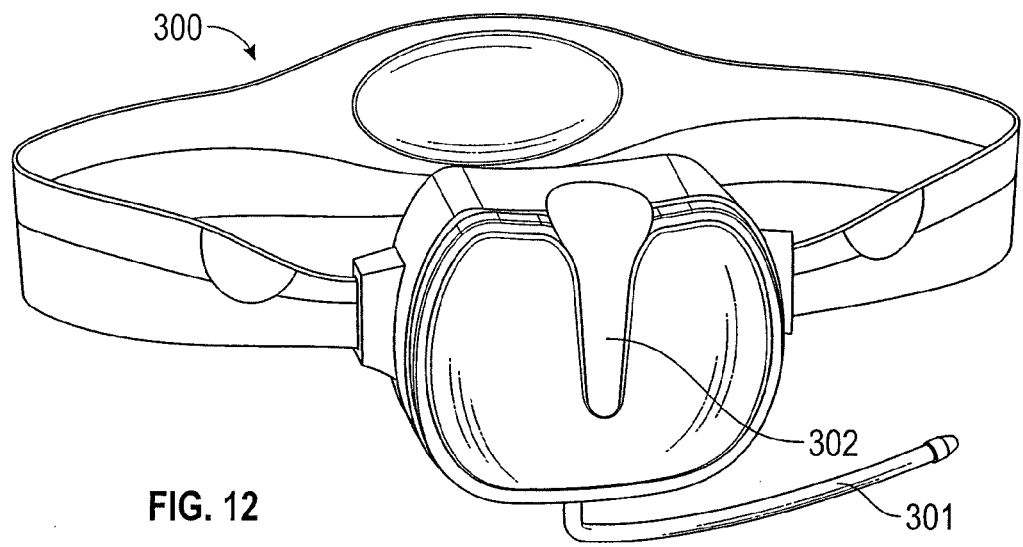
FIG. 12 is a picture of one embodiment of the carrier for the dialysis device/flow system disclosed herein.

Referring now to FIG. 12, there is shown one embodiment of the carrier. (300) for the dialysis device/flow system (302). The dialysis device (302) is attached to a belt like carrier (300) that can be worn around the waist of the user. A tube (304) which exits from the dialysis device/flow system (302), serves a conduit for the dialysate to flow from the peritoneal cavity of the user to the dialysis device (302) and from the dialysis device/flow system (302) back to the peritoneal cavity.

Figure 13:
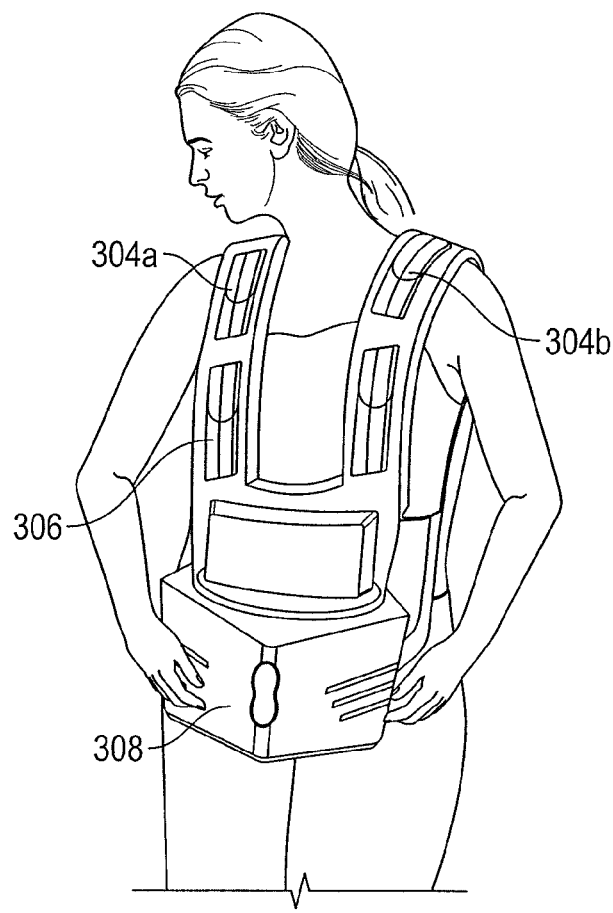
FIG. 13 is a picture of another embodiment of the carrier in the form of a vest for the dialysis device/flow system disclosed herein.

Referring to FIG. 13, there is shown a picture of another embodiment of the carrier in the form of a vest (306) for the dialysis device/flow system (308). The dialysis device/flow system (308) is attached to a vest like carrier (306) having two straps (304a, 304b) that runs over the users shoulder. The straps (304a, 304b) support the entire dialysis device/flow system and distribute the weight of the dialysis device/flow system (308) across both shoulders of the patient.

Figure 14A:
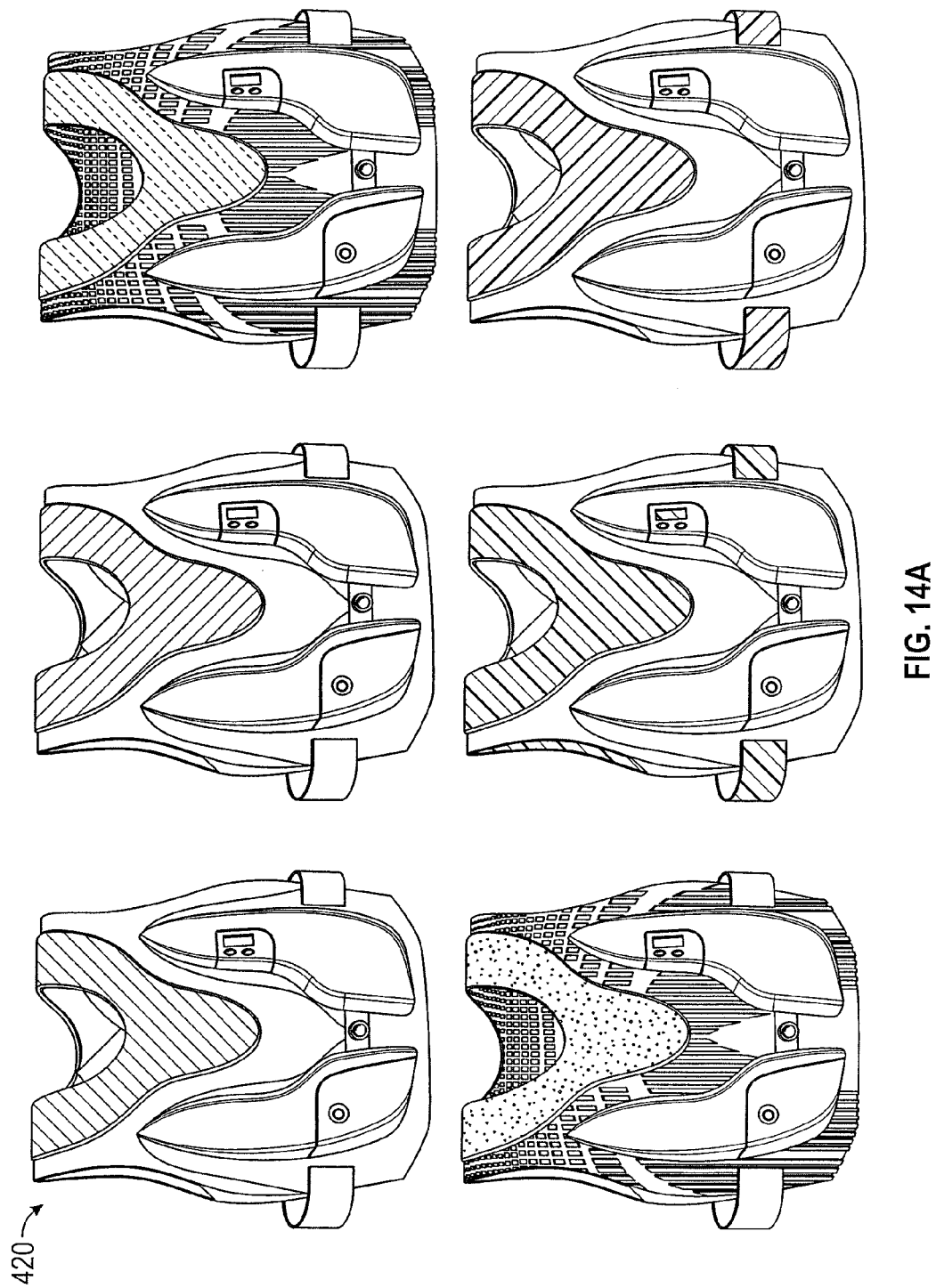
FIG. 14a and FIG. 14b are CAD (Computer Aided Drawings) of another embodiment of the carrier in the form of a vest for the dialysis device/flow system disclosed herein.
Figure 14B:
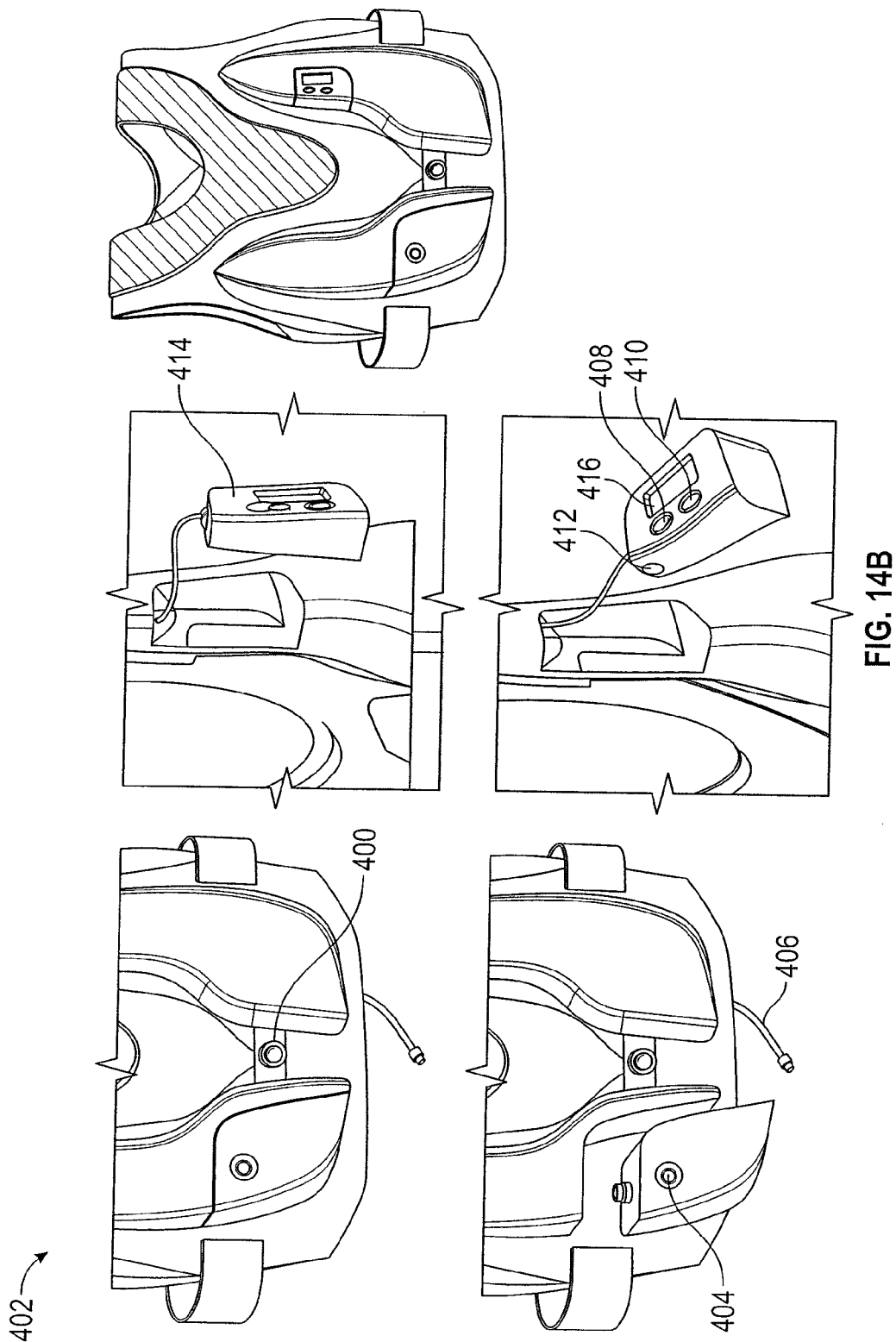

Referring now to FIG. 14a and FIG. 14b, there is shown CAD (computer aided drawings) of another embodiment of the carrier in the form of a vest for the dialysis device/flow system disclosed herein. As shown in FIG. 13b, a button (400) is located on the carrier (420) to disengage the connector holding the dialysis device/flow system in place and in contact with patient's torso. Button (404) located on one side of the carrier (420) serves to disengage a disposable module from the carrier (420). The carrier also comprises a female connector (406) to act as a fluid conduit to and from the patient's peritoneal cavity for dialysis. For the ease of the patient's use, the carrier (420) houses a removable electronic control panel (414) having an on/off button (408), toggle button (410), intermittent alarm (412) and an LCD screen (416) to indicate for instance ammonia or pressure abnormalities. Advantageously, the control panel (414) has a simple interface that is user friendly. More 5. advantageously, this allows ease of use for the elderly and those on the move. The carrier (420) on its own also provides insulation to the dialysis, ensuring that the atmospheric temperature does not adversely affect the temperature of the dialysate. The carrier (420) is also sufficiently hard to protect the components and tubings of the dialysis device/flow system from knocks and accidental pinching. The carrier (420) is also light weight, fire resistant and water proof (non-water absorbing). Moreover, the carrier (420) is ergonomically designed with weight evenly distributed to prevent pressure points and strain on the body. The overall weight of the carrier (420) and the dialysis device/flow system ranges from 2.5 kg to 3.5 kg.

When in use, a patient wears the vest/carrier (420) having two modules (not shown) mounted onto it. The patient then attaches the female connector (406) from the carrier (420) to another male connector (not shown) exiting from the peritoneal cavity. After which, the dialysis device is switched on using the on/off button (408). The LCD screen (416.) then lights up to indicate that the dialysis device/flow system is switched on. Typically the sorbent module is designed to be changed or recharged after eight hours of usage. The beep alarm (412) will sound 2 hours before, followed by 1 hour and 15 minutes before the designated eight hours of usage, to alert the patient to change the spent sorbent. To change the spent sorbent, the patient first switches off the dialysis device/flow system using the on/off button (408). The spent sorbent is then removed from the carrier (420) by using the disengaging button (404). A new sorbent is replaced and the patients starts the machine again.

Applications

The disclosed flow system may be used for peritoneal dialysis or hemodialysis. Advantageously, the flow system only requires the one pump. Advantageously, as only one pump is required to work the flow system in a dialysis device, the overall weight and size of the dialysis device is reduced from conventional dialysis systems. This again improves portability of the dialysis device and patients' mobility. More advantageously, as only one pump is required, the overall power consumption is required to work the flow system of the dialysis device is reduced. This relates to the use of less power storage devices such as batteries, which in turn reduces the overall weight of the device and the weight that the user has to bear. In addition the requirement of less power to function the flow system of the dialysis device prolongs the duration of the power storage devices usage before the next power storage device are recharged or replaced. Advantageously, this reduces the hassle of recharging or replacing the power storage devices frequently.

While reasonable efforts have been employed to describe equivalent embodiments of the present invention, it will be apparent to the person skilled in the art after reading the foregoing disclosure, that various other modifications and adaptations of the invention may be made therein without departing from the spirit and scope of the invention and it is intended that all such modifications and adaptations come within the scope of the appended claims.

The invention claimed is:

1. A flow system of a dialysis device comprising:
    a single dialysate conduit which is capable of being in fluid communication with a peritoneal cavity of a patient's body and of being in fluid communication with a flow path, said flow path allowing dialysate to flow from the patient's body to a sorbent capable of removing contaminants within said dialysate in an outflow mode and in an inflow mode returning said dialysate substantially free of contaminants to said patient's body;
    a single pump for moving said dialysate along said flow path in both the outflow mode and inflow mode;
    a plurality of valves disposed along said flow path and being configured to, in the outflow mode, allow said dialysate to flow from said dialysate conduit to said sorbent for removal of contaminants therein, and in the inflow mode, allow dialysate substantially free of said contaminants to flow back to said dialysate conduit for transmission to said patient's body; and
    a storage module in fluid communication with said flow path,
    said storage module configured to store dialysate that is substantially free of contaminants which have been removed by said sorbent,
    wherein the dialysate flows through the sorbent in the outflow mode and dialysate substantially free of contaminants does not flow through the sorbent in the inflow mode.

2. The flow system as claimed in claim 1, wherein said flow system comprises only one pump that is operative for both the inflow mode and the outflow mode.

3. The flow system as claimed in claim 1 further comprising:
    a fibrin filter means disposed along the flow path to, in an outflow mode, remove fibrin from dialysate before said dialysate enters said pump, said plurality of valves and said sorbent.

4. The flow system as claimed in claim 3, wherein the fibrin filter means is disposed on said flow path adjacent to said dialysate conduit.

5. The flow system as claimed in claim 1, further comprising:
    a micro-organism filter means being disposed along said flow path, said micro-organism filter means being configured to remove microorganisms from the dialysate when transmitted along the flow path.

6. The flow system as claimed in claim 5, wherein the micro-organism filter means is disposed along the flow path between the pump and dialysate conduit.

7. The flow system as claimed in claim 1, further comprising:
    a pump module having said pump and part of said flow path disposed therein, said pump module being capable of being coupled to the patient's body; and
    a sorbent module capable of being reversibly attached to the pump module and having the sorbent and the other part of the flow path disposed therein,
    wherein when the sorbent module is attached to said pump module, the flow path of the sorbent module is in fluid communication with the flow path of the pump module.

8. The flow system as claimed in claim 7, wherein the storage module is disposed in the sorbent module.

9. The flow system as claimed in claim 1, further comprising gas vent means disposed along said flow path for removing gas from the dialysate.

10. The flow system as claimed in claim 9, wherein the gas vent means comprises a sorbent gas vent downstream of the sorbent in the outflow mode, for removing gas from the dialysate that has been generated by contact with the sorbent.

11. The flow system as claimed in claim 10, wherein the sorbent gas vent is disposed within said sorbent module and is in fluid communication with the flow path therein.

12. The flow system as claimed in claim 9, wherein the gas vent means comprises a degasser, upstream of the micro-organism filter means in the inflow mode, for removing gas from the dialysate before passing to said micro-organism filter means.

13. The flow system as claimed in claim 12, wherein the degasser is disposed within said pump module and is in fluid communication with the flow path therein.

14. The flow system as claimed in claim 1, further comprising a controller
    that is configured to actuate the pump for operation in the inflow mode and outflow mode.

15. The flow system as claimed in claim 14, wherein said controller is configured to actuate the plurality of valves for transmission of dialysate along said flow path.

16. The flow system as claimed in claim 15, wherein said valves are selected from the group consisting of at least one of a pinch valve, a shuttle valve, a piloted valve and a solenoid valve.

17. The flow system as claimed in claim 14, comprising a sensor for sensing the amount of dialysate being transmitted from the dialysate conduit in at least one of the inflow mode and outflow mode.

18. The flow system as claimed in claim 17, wherein the controller is configured to determine the amount of dialysate being sensed by the sensor and thereby change the speed of the operation of the pump according to the sensed dialysate load.

19. The flow system as claimed in claim 1, wherein said plurality of valves are operative by the flow direction of dialysate along said flow path.

20. The flow system as claimed in claim 19, wherein said valves are check valves.

21. The flow system as claimed in claim 1, wherein said pump is configured to move dialysate along the flow path without any moving parts of the pump coming into contact with the dialysate.

22. The flow system as claimed in claim 21, wherein said pump is at least one of a peristaltic pump and a diaphragm pump.

23. The flow system as claimed in claim 21, wherein the pump is capable of achieving a dialysate flow rate of from 0.1 l/hr to 20 l/hr.

24. The flow system as claimed in claim 1, further comprising an additive dispensing means for dispensing a desired additive into the dialysate.

25. The flow system as claimed in claim 1, further comprising an ammonia sensor configured to detect ammonia present in said dialysate before passage to said dialysate conduit in an inflow mode.

26. The flow system as claimed in claim 1, wherein the dialysate conduit comprises an outflow conduit for transmission of dialysate from said patient's body and an inflow conduit for transmission of dialysate to said patient's body.

* * * * *